(12) United States Patent
Naito et al.

(10) Patent No.: US 7,217,539 B2
(45) Date of Patent: May 15, 2007

(54) CELL DEATH INDUCERS FOR MAST CELLS

(75) Inventors: Koji Naito, Tokyo (JP); Shusei Uno, Tokyo (JP); Eiji Asakura, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 238 days.

(21) Appl. No.: 10/482,793

(22) PCT Filed: Jul. 4, 2002

(86) PCT No.: PCT/JP02/06790

§ 371 (c)(1),
(2), (4) Date: May 28, 2004

(87) PCT Pub. No.: WO03/004047

PCT Pub. Date: Jan. 16, 2003

(65) Prior Publication Data

US 2004/0248787 A1    Dec. 9, 2004

(30) Foreign Application Priority Data

Jul. 5, 2001    (JP)    ............................. 2001-204567

(51) Int. Cl.
C12P 21/06    (2006.01)
C07H 17/00    (2006.01)
C07K 14/00    (2006.01)

(52) U.S. Cl. .................. 435/69.1; 435/325; 435/252.3; 435/320.1; 536/23.1; 530/350

(58) Field of Classification Search ................ 530/350; 435/69.1, 252.3, 320.1, 325; 536/23.1
See application file for complete search history.

(56) References Cited

FOREIGN PATENT DOCUMENTS

WO    WO 01/66735 A1    9/2001

OTHER PUBLICATIONS

Supplementary Partial European Search Report for EP 02 74 3832 dated Mar. 1, 2005.
Tsujimura et al., "Involvement of Transcription Factor Encoded by the Mouse *mi* Locus (MITF) in Apoptosis of Cultured Mast Cells Induced by Removal of Interleukin-3," American Journal of Pathology, vol. 151, No. 4, pp. 1043-1051 (Oct. 1997).
Nagahara et al., "Transduction of Full-Length TAT Fusion Proteins into Mammalian Cells: TAT-p27$^{Kip1}$ Induces Cell Migration," Nature Medicine, vol. 4, No. 12, pp. 1449-1452 (Dec. 1998).
Kitamura et al., "*mi*-Transcription Factor as a Regulator of Mast Cell Differentiation," International Journal of Hematology, vol. 71, No. 3, pp. 197-202 (Apr. 2000).
Hodgkinson, et al., "Microphthalmia-Associated Transcription Factor," 4 pages (Oct. 1, 2000) (Abstract).

*Primary Examiner*—Karen Cochrane Carlson
(74) *Attorney, Agent, or Firm*—Kilyk & Bowersox, P.L.L.C.

(57) ABSTRACT

A cell death inducer for mast cells, a preventive/therapeutic agent for diseases in which mast cells are implicated, having a fusion protein including a PTD and an MITF variant as an active ingredient and a fusion protein comprises a His Tag, a PTD, and an MITF variant, wherein the MITF variant being an MITF mi variant, wh variant, HLH fragment, or A-type N-terminal region (1-305) fragment, and the PTD being a TAT-derived peptide; DNA coding for the fusion protein; and a method for preparing the fusion protein using genetic engineering techniques. Actions of the fusion protein of the present invention include inhibiting an activity of endogenous MITF by translocating into mast cells, inhibiting a survival of mast cells derived from precursor cells, and inducing cell death (apoptosis) in mature mast cells.

40 Claims, 4 Drawing Sheets

SEQUENCE LISTING

<160> NUMBER OF SEQ ID NOS: 29

<210> SEQ ID NO 1
<211> LENGTH: 415
<212> TYPE: PRT
<213> ORGANISM: Mus musculus
<220> FEATURE:
<221> NAME/KEY: misc_feature
<223> OTHER INFORMATION: MITF mi mutant

<400> SEQUENCE: 1

```
Met Leu Glu Tyr Ser His Tyr Gln Val Gln Thr His Leu Glu Asn Pro
1               5                   10                  15

Thr Lys Tyr His Ile Gln Gln Ala Gln Arg His Gln Val Lys Gln Tyr
            20                  25                  30

Leu Ser Thr Thr Leu Ala Asn Lys His Ala Ser Gln Val Leu Ser Ser
        35                  40                  45

Pro Cys Pro Asn Gln Pro Gly Asp His Ala Met Pro Pro Val Pro Gly
    50                  55                  60

Ser Ser Ala Pro Asn Ser Pro Met Ala Met Leu Thr Leu Asn Ser Asn
65                  70                  75                  80

Cys Glu Lys Glu Ala Phe Tyr Lys Phe Glu Glu Gln Ser Arg Ala Glu
                85                  90                  95

Ser Glu Cys Pro Gly Met Asn Thr His Ser Arg Ala Ser Cys Met Gln
            100                 105                 110

Met Asp Asp Val Ile Asp Ile Ile Ser Leu Glu Ser Ser Tyr Asn
        115                 120                 125

Glu Glu Ile Leu Gly Leu Met Asp Pro Ala Leu Gln Met Ala Asn Thr
    130                 135                 140

Leu Pro Val Ser Gly Asn Leu Ile Asp Leu Tyr Ser Asn Gln Gly Leu
145                 150                 155                 160

Pro Pro Pro Gly Leu Thr Ile Ser Asn Ser Cys Pro Ala Asn Leu Pro
                165                 170                 175

Asn Ile Lys Arg Glu Leu Thr Ala Cys Ile Phe Pro Thr Glu Ser Glu
            180                 185                 190

Ala Arg Ala Leu Ala Lys Glu Arg Gln Lys Lys Asp Asn His Asn Leu
        195                 200                 205

Ile Glu Arg Arg Arg Phe Asn Ile Asn Asp Arg Ile Lys Glu Leu Gly
    210                 215                 220

Thr Leu Ile Pro Lys Ser Asn Asp Pro Asp Met Arg Trp Asn Lys Gly
225                 230                 235                 240

Thr Ile Leu Lys Ala Ser Val Asp Tyr Ile Arg Lys Leu Gln Arg Glu
                245                 250                 255

Gln Gln Arg Ala Lys Asp Leu Glu Asn Arg Gln Lys Lys Leu Glu His
            260                 265                 270

Ala Asn Arg His Leu Leu Leu Arg Val Gln Glu Leu Glu Met Gln Ala
        275                 280                 285

Arg Ala His Gly Leu Ser Leu Ile Pro Ser Thr Gly Leu Cys Ser Pro
    290                 295                 300

Asp Leu Val Asn Arg Ile Ile Lys Gln Glu Pro Val Leu Glu Asn Cys
305                 310                 315                 320

Ser Gln Glu Leu Val Gln His Gln Ala Asp Leu Thr Cys Thr Thr Thr
                325                 330                 335

Leu Asp Leu Thr Asp Gly Thr Ile Thr Phe Thr Asn Asn Leu Gly Thr
```

```
                    340             345             350
Met Pro Glu Ser Ser Pro Ala Tyr Ser Ile Pro Arg Lys Met Gly Ser
                355             360             365

Asn Leu Glu Asp Ile Leu Met Asp Asp Ala Leu Ser Pro Val Gly Val
            370             375             380

Thr Asp Pro Leu Leu Ser Ser Val Ser Pro Gly Ala Ser Lys Thr Ser
385             390             395             400

Ser Arg Arg Ser Ser Met Ser Ala Glu Glu Thr Glu His Ala Cys
                405             410             415

<210> SEQ ID NO 2
<211> LENGTH: 1248
<212> TYPE: DNA
<213> ORGANISM: Mus musculus
<220> FEATURE:
<221> NAME/KEY: misc_feature
<223> OTHER INFORMATION: DNA coding MITF mi mutant
<220> FEATURE:
<221> NAME/KEY: CDS
<222> LOCATION: (1)..(1248)

<400> SEQUENCE: 2 atg cta gaa tac agt cac tac cag gtg cag acc cac ctg gaa aac ccc      48
Met Leu Glu Tyr Ser His Tyr Gln Val Gln Thr His Leu Glu Asn Pro
1               5                   10                  15 acc aag tac cac ata cag caa gct cag agg cac cag gta aag cag tac      96
Thr Lys Tyr His Ile Gln Gln Ala Gln Arg His Gln Val Lys Gln Tyr
                20                  25                  30 ctt tct acc act tta gca aat aaa cat gcc agc caa gtc ctg agc tca     144
Leu Ser Thr Thr Leu Ala Asn Lys His Ala Ser Gln Val Leu Ser Ser
            35                  40                  45 cca tgt cca aac cag cct ggc gac cat gcc atg cca cca gtg ccg ggg     192
Pro Cys Pro Asn Gln Pro Gly Asp His Ala Met Pro Pro Val Pro Gly
        50                  55                  60 agc agc gca ccc aac agc cct atg gct atg ctc act ctt aac tcc aac     240
Ser Ser Ala Pro Asn Ser Pro Met Ala Met Leu Thr Leu Asn Ser Asn
65                  70                  75                  80 tgt gaa aaa gag gca ttt tat aag ttt gag gag cag agc agg gca gag     288
Cys Glu Lys Glu Ala Phe Tyr Lys Phe Glu Glu Gln Ser Arg Ala Glu
                85                  90                  95 agt gag tgc cca ggt atg aac acg cac tct cga gcg tcg tgc atg cag     336
Ser Glu Cys Pro Gly Met Asn Thr His Ser Arg Ala Ser Cys Met Gln
                100                 105                 110 atg gat gat gta att gat gac atc atc agc ctg gaa tca agt tat aat     384
Met Asp Asp Val Ile Asp Asp Ile Ile Ser Leu Glu Ser Ser Tyr Asn
            115                 120                 125 gaa gaa att ttg ggc ttg atg gat ccg gcc ttg caa atg gca aat acg     432
Glu Glu Ile Leu Gly Leu Met Asp Pro Ala Leu Gln Met Ala Asn Thr
        130                 135                 140 tta ccc gtc tct gga aac ttg atc gac ctc tac agc aac cag ggc ctg     480
Leu Pro Val Ser Gly Asn Leu Ile Asp Leu Tyr Ser Asn Gln Gly Leu
145                 150                 155                 160 cca ccg cca ggc ctt acc atc agc aac tcc tgt cca gcc aac ctt ccc     528
Pro Pro Pro Gly Leu Thr Ile Ser Asn Ser Cys Pro Ala Asn Leu Pro
                165                 170                 175 aac ata aaa agg gag ctc aca gcg tgt att ttc ccc aca gag tct gaa     576
Asn Ile Lys Arg Glu Leu Thr Ala Cys Ile Phe Pro Thr Glu Ser Glu
                180                 185                 190 gca aga gca ttg gct aaa gag agg cag aaa aag gac aat cac aac ttg     624
Ala Arg Ala Leu Ala Lys Glu Arg Gln Lys Lys Asp Asn His Asn Leu
            195                 200                 205
```

```
att gaa cga aga aga ttt aac ata aac gac cgc att aag gag cta ggt    672
Ile Glu Arg Arg Arg Phe Asn Ile Asn Asp Arg Ile Lys Glu Leu Gly
    210                 215                 220 act ctg atc ccc aag tca aat gat cca gac atg cgg tgg aac aag gga    720
Thr Leu Ile Pro Lys Ser Asn Asp Pro Asp Met Arg Trp Asn Lys Gly
225                 230                 235                 240 acc att ctc aag gcc tct gtg gac tac atc cgg aag ttg caa cgg gaa    768
Thr Ile Leu Lys Ala Ser Val Asp Tyr Ile Arg Lys Leu Gln Arg Glu
                245                 250                 255 cag caa cga gct aag gac ctt gaa aac cga cag aag aag ctg gag cat    816
Gln Gln Arg Ala Lys Asp Leu Glu Asn Arg Gln Lys Lys Leu Glu His
            260                 265                 270 gcg aac cgg cac ctg ctc ctc aga gta cag gag ctg gag atg cag gct    864
Ala Asn Arg His Leu Leu Leu Arg Val Gln Glu Leu Glu Met Gln Ala
        275                 280                 285 aga gcg cat gga ctt tcc ctt atc cca tcc acc ggt ctc tgc tcg cct    912
Arg Ala His Gly Leu Ser Leu Ile Pro Ser Thr Gly Leu Cys Ser Pro
    290                 295                 300 gat ctg gtg aat cgg atc atc aag caa gaa cca gtt ctt gag aac tgc    960
Asp Leu Val Asn Arg Ile Ile Lys Gln Glu Pro Val Leu Glu Asn Cys
305                 310                 315                 320 agc cag gaa ctt gta cag cac cag gca gac ctg aca tgt acg aca act   1008
Ser Gln Glu Leu Val Gln His Gln Ala Asp Leu Thr Cys Thr Thr Thr
                325                 330                 335 ctg gat ctc acg gac ggt acc atc acc ttt acc aac aac ctc ggc acc   1056
Leu Asp Leu Thr Asp Gly Thr Ile Thr Phe Thr Asn Asn Leu Gly Thr
            340                 345                 350 atg ccg gag agc agc ccg gcc tac agc atc ccc agg aag atg ggc tcc   1104
Met Pro Glu Ser Ser Pro Ala Tyr Ser Ile Pro Arg Lys Met Gly Ser
        355                 360                 365 aac ttg gaa gac atc ctg atg gac gat gcc ctc tca cct gtt gga gtc   1152
Asn Leu Glu Asp Ile Leu Met Asp Asp Ala Leu Ser Pro Val Gly Val
    370                 375                 380 acc gac cca ctg ctg tca tca gtg tcg cca gga gct tca aaa aca agc   1200
Thr Asp Pro Leu Leu Ser Ser Val Ser Pro Gly Ala Ser Lys Thr Ser
385                 390                 395                 400 agc cgg agg agc agt atg agc gca gaa gaa acg gag cat gcg tgt tag   1248
Ser Arg Arg Ser Ser Met Ser Ala Glu Glu Thr Glu His Ala Cys
                405                 410                 415
```

<210> SEQ ID NO 3
<211> LENGTH: 410
<212> TYPE: PRT
<213> ORGANISM: Mus musculus
<220> FEATURE:
<221> NAME/KEY: misc_feature
<223> OTHER INFORMATION: MITF wh mutant

<400> SEQUENCE: 3

```
Met Leu Glu Tyr Ser His Tyr Gln Val Gln Thr His Leu Glu Asn Pro
1               5                   10                  15

Thr Lys Tyr His Ile Gln Gln Ala Gln Arg His Gln Val Lys Gln Tyr
            20                  25                  30

Leu Ser Thr Thr Leu Ala Asn Lys His Ala Ser Gln Val Leu Ser Ser
        35                  40                  45

Pro Cys Pro Asn Gln Pro Gly Asp His Ala Met Pro Pro Val Pro Gly
    50                  55                  60

Ser Ser Ala Pro Asn Ser Pro Met Ala Met Leu Thr Leu Asn Ser Asn
65                  70                  75                  80
```

```
Cys Glu Lys Glu Ala Phe Tyr Lys Phe Glu Glu Gln Ser Arg Ala Glu
                85                  90                  95
Ser Glu Cys Pro Gly Met Asn Thr His Ser Arg Ala Ser Cys Met Gln
            100                 105                 110
Met Asp Asp Val Ile Asp Ile Ile Ser Leu Glu Ser Ser Tyr Asn
            115                 120                 125
Glu Glu Ile Leu Gly Leu Met Asp Pro Ala Leu Gln Met Ala Asn Thr
130                 135                 140
Leu Pro Val Ser Gly Asn Leu Ile Asp Leu Tyr Ser Asn Gln Gly Leu
145                 150                 155                 160
Pro Pro Pro Gly Leu Thr Ile Ser Asn Ser Cys Pro Ala Asn Leu Pro
                165                 170                 175
Asn Ile Lys Arg Glu Leu Thr Glu Ser Glu Ala Arg Ala Leu Ala Lys
                180                 185                 190
Glu Arg Gln Lys Lys Asp Asn His Asn Leu Asn Glu Arg Arg Arg Arg
                195                 200                 205
Phe Asn Ile Asn Asp Arg Ile Lys Glu Leu Gly Thr Leu Ile Pro Lys
210                 215                 220
Ser Asn Asp Pro Asp Met Arg Trp Asn Lys Gly Thr Ile Leu Lys Ala
225                 230                 235                 240
Ser Val Asp Tyr Ile Arg Lys Leu Gln Arg Glu Gln Gln Arg Ala Lys
                245                 250                 255
Asp Leu Glu Asn Arg Gln Lys Lys Leu Glu His Ala Asn Arg His Leu
                260                 265                 270
Leu Leu Arg Val Gln Glu Leu Glu Met Gln Ala Arg Ala His Gly Leu
                275                 280                 285
Ser Leu Ile Pro Ser Thr Gly Leu Cys Ser Pro Asp Leu Val Asn Arg
290                 295                 300
Ile Ile Lys Gln Glu Pro Val Leu Glu Asn Cys Ser Gln Glu Leu Val
305                 310                 315                 320
Gln His Gln Ala Asp Leu Thr Cys Thr Thr Thr Leu Asp Leu Thr Asp
                325                 330                 335
Gly Thr Ile Thr Phe Thr Asn Asn Leu Gly Thr Met Pro Glu Ser Ser
                340                 345                 350
Pro Ala Tyr Ser Ile Pro Arg Lys Met Gly Ser Asn Leu Glu Asp Ile
                355                 360                 365
Leu Met Asp Asp Ala Leu Ser Pro Val Gly Val Thr Asp Pro Leu Leu
370                 375                 380
Ser Ser Val Ser Pro Gly Ala Ser Lys Thr Ser Ser Arg Arg Ser Ser
385                 390                 395                 400
Met Ser Ala Glu Glu Thr Glu His Ala Cys
                405                 410

<210> SEQ ID NO 4
<211> LENGTH: 1233
<212> TYPE: DNA
<213> ORGANISM: Mus musculus
<220> FEATURE:
<221> NAME/KEY: misc_feature
<223> OTHER INFORMATION: DNA coding MITF wh mutant
<220> FEATURE:
<221> NAME/KEY: CDS
<222> LOCATION: (1)..(1233)

<400> SEQUENCE: 4 atg cta gaa tac agt cac tac cag gtg cag acc cac ctg gaa aac ccc      48
Met Leu Glu Tyr Ser His Tyr Gln Val Gln Thr His Leu Glu Asn Pro
```

```
                                -continued
1               5              10             15 acc aag tac cac ata cag caa gct cag agg cac cag gta aag cag tac      96
Thr Lys Tyr His Ile Gln Gln Ala Gln Arg His Gln Val Lys Gln Tyr
             20              25              30 ctt tct acc act tta gca aat aaa cat gcc agc caa gtc ctg agc tca     144
Leu Ser Thr Thr Leu Ala Asn Lys His Ala Ser Gln Val Leu Ser Ser
         35              40              45 cca tgt cca aac cag cct ggc gac cat gcc atg cca cca gtg ccg ggg     192
Pro Cys Pro Asn Gln Pro Gly Asp His Ala Met Pro Pro Val Pro Gly
     50              55              60 agc agc gca ccc aac agc cct atg gct atg ctc act ctt aac tcc aac     240
Ser Ser Ala Pro Asn Ser Pro Met Ala Met Leu Thr Leu Asn Ser Asn
 65              70              75              80 tgt gaa aaa gag gca ttt tat aag ttt gag gag cag agc agg gca gag     288
Cys Glu Lys Glu Ala Phe Tyr Lys Phe Glu Glu Gln Ser Arg Ala Glu
                 85              90              95 agt gag tgc cca ggt atg aac acg cac tct cga gcg tcg tgc atg cag     336
Ser Glu Cys Pro Gly Met Asn Thr His Ser Arg Ala Ser Cys Met Gln
             100             105             110 atg gat gat gta att gat gac atc atc agc ctg gaa tca agt tat aat     384
Met Asp Asp Val Ile Asp Asp Ile Ile Ser Leu Glu Ser Ser Tyr Asn
         115             120             125 gaa gaa att ttg ggc ttg atg gat ccg gcc ttg caa atg gca aat acg     432
Glu Glu Ile Leu Gly Leu Met Asp Pro Ala Leu Gln Met Ala Asn Thr
     130             135             140 tta ccc gtc tct gga aac ttg atc gac ctc tac agc aac cag ggc ctg     480
Leu Pro Val Ser Gly Asn Leu Ile Asp Leu Tyr Ser Asn Gln Gly Leu
145             150             155             160 cca ccg cca ggc ctt acc atc agc aac tcc tgt cca gcc aac ctt ccc     528
Pro Pro Pro Gly Leu Thr Ile Ser Asn Ser Cys Pro Ala Asn Leu Pro
                 165             170             175 aac ata aaa agg gag ctc aca gag tct gaa gca aga gca ttg gct aaa     576
Asn Ile Lys Arg Glu Leu Thr Glu Ser Glu Ala Arg Ala Leu Ala Lys
             180             185             190 gag agg cag aaa aag gac aat cac aac ttg aat gaa cga aga aga aga     624
Glu Arg Gln Lys Lys Asp Asn His Asn Leu Asn Glu Arg Arg Arg Arg
         195             200             205 ttt aac ata aac gac cgc att aag gag cta ggt act ctg atc ccc aag     672
Phe Asn Ile Asn Asp Arg Ile Lys Glu Leu Gly Thr Leu Ile Pro Lys
     210             215             220 tca aat gat cca gac atg cgg tgg aac aag gga acc att ctc aag gcc     720
Ser Asn Asp Pro Asp Met Arg Trp Asn Lys Gly Thr Ile Leu Lys Ala
225             230             235             240 tct gtg gac tac atc cgg aag ttg caa cgg gaa cag caa cga gct aag     768
Ser Val Asp Tyr Ile Arg Lys Leu Gln Arg Glu Gln Gln Arg Ala Lys
                 245             250             255 gac ctt gaa aac cga cag aag aag ctg gag cat gcg aac cgg cac ctg     816
Asp Leu Glu Asn Arg Gln Lys Lys Leu Glu His Ala Asn Arg His Leu
             260             265             270 ctg ctc aga gta cag gag ctg gag atg cag gct aga gcg cat gga ctt     864
Leu Leu Arg Val Gln Glu Leu Glu Met Gln Ala Arg Ala His Gly Leu
         275             280             285 tcc ctt atc cca tcc acc ggt ctc tgc tcg cct gat ctg gtg aat cgg     912
Ser Leu Ile Pro Ser Thr Gly Leu Cys Ser Pro Asp Leu Val Asn Arg
     290             295             300 atc atc aag caa gaa cca gtt ctt gag aac tgc agc cag gaa ctt gta     960
Ile Ile Lys Gln Glu Pro Val Leu Glu Asn Cys Ser Gln Glu Leu Val
305             310             315             320 cag cac cag gca gac ctg aca tgt acg aca act ctg gat ctc acg gac    1008
Gln His Gln Ala Asp Leu Thr Cys Thr Thr Thr Leu Asp Leu Thr Asp
```

```
                                                                                       -continued
Gln His Gln Ala Asp Leu Thr Cys Thr Thr Thr Leu Asp Leu Thr Asp
            325                 330                 335 ggt acc atc acc ttt acc aac aac ctc ggc acc atg ccg gag agc agc        1056
Gly Thr Ile Thr Phe Thr Asn Asn Leu Gly Thr Met Pro Glu Ser Ser
            340                 345                 350 ccg gcc tac agc atc ccc agg aag atg ggc tcc aac ttg gaa gac atc        1104
Pro Ala Tyr Ser Ile Pro Arg Lys Met Gly Ser Asn Leu Glu Asp Ile
            355                 360                 365 ctg atg gac gat gcc ctc tca cct gtt gga gtc acc gac cca ctg ctg        1152
Leu Met Asp Asp Ala Leu Ser Pro Val Gly Val Thr Asp Pro Leu Leu
    370                 375                 380 tca tca gtg tcg cca gga gct tca aaa aca agc agc cgg agg agc agt        1200
Ser Ser Val Ser Pro Gly Ala Ser Lys Thr Ser Ser Arg Arg Ser Ser
385                 390                 395                 400 atg agc gca gaa gaa acg gag cat gcg tgt tag                            1233
Met Ser Ala Glu Glu Thr Glu His Ala Cys
                405                 410

<210> SEQ ID NO 5
<211> LENGTH: 91
<212> TYPE: PRT
<213> ORGANISM: Artificial
<220> FEATURE:
<223> OTHER INFORMATION: Description of Artificial Sequence: MITF
      bHLH-Zip fragment

<400> SEQUENCE: 5

Met Leu Ala Lys Glu Arg Gln Lys Lys Asp Asn His Asn Leu Ile Glu
1               5                   10                  15

Arg Arg Arg Arg Phe Asn Ile Asn Asp Arg Ile Lys Glu Leu Gly Thr
            20                  25                  30

Leu Ile Pro Lys Ser Asn Asp Pro Asp Met Arg Trp Asn Lys Gly Thr
        35                  40                  45

Ile Leu Lys Ala Ser Val Asp Tyr Ile Arg Lys Leu Gln Arg Glu Gln
    50                  55                  60

Gln Arg Ala Lys Asp Leu Glu Asn Arg Gln Lys Lys Leu Glu His Ala
65                  70                  75                  80

Asn Arg His Leu Leu Leu Arg Val Gln Glu Leu
                85                  90

<210> SEQ ID NO 6
<211> LENGTH: 276
<212> TYPE: DNA
<213> ORGANISM: Artificial
<220> FEATURE:
<223> OTHER INFORMATION: Description of Artificial Sequence: DNA coding
      MITF bHLH-Zip fragment
<220> FEATURE:
<221> NAME/KEY: CDS
<222> LOCATION: (1)..(276)

<400> SEQUENCE: 6 atg ttg gct aaa gag agg cag aaa aag gac aat cac aac ttg att gaa         48
Met Leu Ala Lys Glu Arg Gln Lys Lys Asp Asn His Asn Leu Ile Glu
1               5                   10                  15 cga aga aga aga ttt aac ata aac gac cgc att aag gag cta ggt act         96
Arg Arg Arg Arg Phe Asn Ile Asn Asp Arg Ile Lys Glu Leu Gly Thr
            20                  25                  30 ctg atc ccc aag tca aat gat cca gac atg cgg tgg aac aag gga acc        144
Leu Ile Pro Lys Ser Asn Asp Pro Asp Met Arg Trp Asn Lys Gly Thr
        35                  40                  45 att ctc aag gcc tct gtg gac tac atc cgg aag ttg caa cgg gaa cag        192
```

```
Ile Leu Lys Ala Ser Val Asp Tyr Ile Arg Lys Leu Gln Arg Glu Gln
            50                  55                  60 caa cga gct aag gac ctt gaa aac cga cag aag aag ctg gag cat gcg       240
Gln Arg Ala Lys Asp Leu Glu Asn Arg Gln Lys Lys Leu Glu His Ala
 65                  70                  75                  80 aac cgg cac ctg ctg ctc aga gta cag gag ctg tag                       276
Asn Arg His Leu Leu Leu Arg Val Gln Glu Leu
                     85                  90
```

<210> SEQ ID NO 7
<211> LENGTH: 11
<212> TYPE: PRT
<213> ORGANISM: Artificial
<220> FEATURE:
<223> OTHER INFORMATION: Description of Artificial Sequence: TAT-derived
      peptide

<400> SEQUENCE: 7

```
Tyr Gly Arg Lys Lys Arg Arg Gln Arg Arg Arg
 1               5                  10
```

<210> SEQ ID NO 8
<211> LENGTH: 33
<212> TYPE: DNA
<213> ORGANISM: Artificial
<220> FEATURE:
<223> OTHER INFORMATION: Description of Artificial Sequence: DNA coding
      TAT-derived peptide
<220> FEATURE:
<221> NAME/KEY: CDS
<222> LOCATION: (1)..(33)

<400> SEQUENCE: 8

```
tat ggc agg aag aag cgg aga cag cga cga aga                           33
Tyr Gly Arg Lys Lys Arg Arg Gln Arg Arg Arg
 1               5                  10
```

<210> SEQ ID NO 9
<211> LENGTH: 10
<212> TYPE: PRT
<213> ORGANISM: Artificial
<220> FEATURE:
<223> OTHER INFORMATION: Description of Artificial Sequence: HisTag

<400> SEQUENCE: 9

```
Met Gly Gly Ser His His His His His His
 1               5                  10
```

<210> SEQ ID NO 10
<211> LENGTH: 30
<212> TYPE: DNA
<213> ORGANISM: Artificial
<220> FEATURE:
<223> OTHER INFORMATION: Description of Artificial Sequence: DNA coding
      HisTag
<220> FEATURE:
<221> NAME/KEY: CDS
<222> LOCATION: (1)..(30)

<400> SEQUENCE: 10

```
atg ggg ggt tct cat cat cat cat cat cat                               30
Met Gly Gly Ser His His His His His His
 1               5                  10
```

<210> SEQ ID NO 11
<211> LENGTH: 439
<212> TYPE: PRT
<213> ORGANISM: Artificial

-continued

```
<220> FEATURE:
<223> OTHER INFORMATION: Description of Artificial Sequence: fused
      protein composed of HisTag-PTD-MITF mi mutant

<400> SEQUENCE: 11

Met Gly Gly Ser His His His His His Gly Gly Tyr Gly Arg Lys
1               5                   10                  15

Lys Arg Arg Gln Arg Arg Gly Met Leu Glu Tyr Ser His Tyr Gln
            20                  25                  30

Val Gln Thr His Leu Glu Asn Pro Thr Lys Tyr His Ile Gln Gln Ala
            35                  40                  45

Gln Arg His Gln Val Lys Gln Tyr Leu Ser Thr Thr Leu Ala Asn Lys
    50                  55                  60

His Ala Ser Gln Val Leu Ser Ser Pro Cys Pro Asn Gln Pro Gly Asp
65                  70                  75                  80

His Ala Met Pro Pro Val Pro Gly Ser Ser Ala Pro Asn Ser Pro Met
                85                  90                  95

Ala Met Leu Thr Leu Asn Ser Asn Cys Glu Lys Glu Ala Phe Tyr Lys
                100                 105                 110

Phe Glu Glu Gln Ser Arg Ala Glu Ser Glu Cys Pro Gly Met Asn Thr
            115                 120                 125

His Ser Arg Ala Ser Cys Met Gln Met Asp Asp Val Ile Asp Asp Ile
130                 135                 140

Ile Ser Leu Glu Ser Ser Tyr Asn Glu Glu Ile Leu Gly Leu Met Asp
145                 150                 155                 160

Pro Ala Leu Gln Met Ala Asn Thr Leu Pro Val Ser Gly Asn Leu Ile
                165                 170                 175

Asp Leu Tyr Ser Asn Gln Gly Leu Pro Pro Pro Gly Leu Thr Ile Ser
            180                 185                 190

Asn Ser Cys Pro Ala Asn Leu Pro Asn Ile Lys Arg Glu Leu Thr Ala
        195                 200                 205

Cys Ile Phe Pro Thr Glu Ser Glu Ala Arg Ala Leu Ala Lys Glu Arg
    210                 215                 220

Gln Lys Lys Asp Asn His Asn Leu Ile Glu Arg Arg Phe Asn Ile
225                 230                 235                 240

Asn Asp Arg Ile Lys Glu Leu Gly Thr Leu Ile Pro Lys Ser Asn Asp
                245                 250                 255

Pro Asp Met Arg Trp Asn Lys Gly Thr Ile Leu Lys Ala Ser Val Asp
            260                 265                 270

Tyr Ile Arg Lys Leu Gln Arg Glu Gln Gln Arg Ala Lys Asp Leu Glu
        275                 280                 285

Asn Arg Gln Lys Lys Leu Glu His Ala Asn Arg His Leu Leu Leu Arg
    290                 295                 300

Val Gln Glu Leu Glu Met Gln Ala Arg Ala His Gly Leu Ser Leu Ile
305                 310                 315                 320

Pro Ser Thr Gly Leu Cys Ser Pro Asp Leu Val Asn Arg Ile Ile Lys
                325                 330                 335

Gln Glu Pro Val Leu Glu Asn Cys Ser Gln Glu Leu Val Gln His Gln
            340                 345                 350

Ala Asp Leu Thr Cys Thr Thr Thr Leu Asp Leu Thr Asp Gly Thr Ile
        355                 360                 365

Thr Phe Thr Asn Asn Leu Gly Thr Met Pro Glu Ser Ser Pro Ala Tyr
    370                 375                 380

Ser Ile Pro Arg Lys Met Gly Ser Asn Leu Glu Asp Ile Leu Met Asp
```

-continued

```
            385                 390                 395                 400
Asp Ala Leu Ser Pro Val Gly Val Thr Asp Pro Leu Leu Ser Ser Val
                405                 410                 415
Ser Pro Gly Ala Ser Lys Thr Ser Ser Arg Arg Ser Ser Met Ser Ala
            420                 425                 430
Glu Glu Thr Glu His Ala Cys
        435

<210> SEQ ID NO 12
<211> LENGTH: 1320
<212> TYPE: DNA
<213> ORGANISM: Artificial
<220> FEATURE:
<223> OTHER INFORMATION: Description of Artificial Sequence: DNA coding
      the fused protein composed of HisTag-PTD-MITF mi mutant
<220> FEATURE:
<221> NAME/KEY: CDS
<222> LOCATION: (1)..(1320)

<400> SEQUENCE: 12 atg ggg ggt tct cat cat cat cat cat cat ggt ggt tat ggc agg aag        48
Met Gly Gly Ser His His His His His His Gly Gly Tyr Gly Arg Lys
1               5                   10                  15 aag cgg aga cag cga cga aga ggt atg cta gaa tac agt cac tac cag        96
Lys Arg Arg Gln Arg Arg Arg Gly Met Leu Glu Tyr Ser His Tyr Gln
            20                  25                  30 gtg cag acc cac ctg gaa aac ccc acc aag tac cac ata cag caa gct       144
Val Gln Thr His Leu Glu Asn Pro Thr Lys Tyr His Ile Gln Gln Ala
        35                  40                  45 cag agg cac cag gta aag cag tac ctt tct acc act tta gca aat aaa       192
Gln Arg His Gln Val Lys Gln Tyr Leu Ser Thr Thr Leu Ala Asn Lys
    50                  55                  60 cat gcc agc caa gtc ctg agc tca cca tgt cca aac cag cct ggc gac       240
His Ala Ser Gln Val Leu Ser Ser Pro Cys Pro Asn Gln Pro Gly Asp
65                  70                  75                  80 cat gcc atg cca cca gtg ccg ggg agc agc gca ccc aac agc cct atg       288
His Ala Met Pro Pro Val Pro Gly Ser Ser Ala Pro Asn Ser Pro Met
                85                  90                  95 gct atg ctc act ctt aac tcc aac tgt gaa aaa gag gca ttt tat aag       336
Ala Met Leu Thr Leu Asn Ser Asn Cys Glu Lys Glu Ala Phe Tyr Lys
            100                 105                 110 ttt gag gag cag agc agg gca gag agt gag tgc cca ggt atg aac acg       384
Phe Glu Glu Gln Ser Arg Ala Glu Ser Glu Cys Pro Gly Met Asn Thr
        115                 120                 125 cac tct cga gcg tcg tgc atg cag atg gat gat gta att gat gac atc       432
His Ser Arg Ala Ser Cys Met Gln Met Asp Asp Val Ile Asp Asp Ile
    130                 135                 140 atc agc ctg gaa tca agt tat aat gaa gaa att ttg ggc ttg atg gat       480
Ile Ser Leu Glu Ser Ser Tyr Asn Glu Glu Ile Leu Gly Leu Met Asp
145                 150                 155                 160 ccg gcc ttg caa atg gca aat acg tta ccc gtc tct gga aac ttg atc       528
Pro Ala Leu Gln Met Ala Asn Thr Leu Pro Val Ser Gly Asn Leu Ile
                165                 170                 175 gac ctc tac agc aac cag ggc ctg cca ccg cca ggc ctt acc atc agc       576
Asp Leu Tyr Ser Asn Gln Gly Leu Pro Pro Pro Gly Leu Thr Ile Ser
            180                 185                 190 aac tcc tgt cca gcc aac ctt ccc aac ata aaa agg gag ctc aca gcg       624
Asn Ser Cys Pro Ala Asn Leu Pro Asn Ile Lys Arg Glu Leu Thr Ala
        195                 200                 205 tgt att ttc ccc aca gag tct gaa gca aga gca ttg gct aaa gag agg       672
Cys Ile Phe Pro Thr Glu Ser Glu Ala Arg Ala Leu Ala Lys Glu Arg
```

-continued

```
            210                 215                 220
cag aaa aag gac aat cac aac ttg att gaa cga aga aga ttt aac ata      720
Gln Lys Lys Asp Asn His Asn Leu Ile Glu Arg Arg Arg Phe Asn Ile
225                 230                 235                 240 aac gac cgc att aag gag cta ggt act ctg atc ccc aag tca aat gat      768
Asn Asp Arg Ile Lys Glu Leu Gly Thr Leu Ile Pro Lys Ser Asn Asp
                245                 250                 255 cca gac atg cgg tgg aac aag gga acc att ctc aag gcc tct gtg gac      816
Pro Asp Met Arg Trp Asn Lys Gly Thr Ile Leu Lys Ala Ser Val Asp
            260                 265                 270 tac atc cgg aag ttg caa cgg gaa cag caa cga gct aag gac ctt gaa      864
Tyr Ile Arg Lys Leu Gln Arg Glu Gln Gln Arg Ala Lys Asp Leu Glu
        275                 280                 285 aac cga cag aag aag ctg gag cat gcg aac cgg cac ctg ctc ctc aga      912
Asn Arg Gln Lys Lys Leu Glu His Ala Asn Arg His Leu Leu Leu Arg
    290                 295                 300 gta cag gag ctg gag atg cag gct aga gcg cat gga ctt tcc ctt atc      960
Val Gln Glu Leu Glu Met Gln Ala Arg Ala His Gly Leu Ser Leu Ile
305                 310                 315                 320 cca tcc acc ggt ctc tgc tcg cct gat ctg gtg aat cgg atc atc aag     1008
Pro Ser Thr Gly Leu Cys Ser Pro Asp Leu Val Asn Arg Ile Ile Lys
                325                 330                 335 caa gaa cca gtt ctt gag aac tgc agc cag gaa ctt gta cag cac cag     1056
Gln Glu Pro Val Leu Glu Asn Cys Ser Gln Glu Leu Val Gln His Gln
            340                 345                 350 gca gac ctg aca tgt acg aca act ctg gat ctc acg gac ggt acc atc     1104
Ala Asp Leu Thr Cys Thr Thr Thr Leu Asp Leu Thr Asp Gly Thr Ile
        355                 360                 365 acc ttt acc aac aac ctc ggc acc atg ccg gag agc agc ccg gcc tac     1152
Thr Phe Thr Asn Asn Leu Gly Thr Met Pro Glu Ser Ser Pro Ala Tyr
    370                 375                 380 agc atc ccc agg aag atg ggc tcc aac ttg gaa gac atc ctg atg gac     1200
Ser Ile Pro Arg Lys Met Gly Ser Asn Leu Glu Asp Ile Leu Met Asp
385                 390                 395                 400 gat gcc ctc tca cct gtt gga gtc acc gac cca ctg ctg tca tca gtg     1248
Asp Ala Leu Ser Pro Val Gly Val Thr Asp Pro Leu Leu Ser Ser Val
                405                 410                 415 tcg cca gga gct tca aaa aca agc agc cgg agg agc agt atg agc gca     1296
Ser Pro Gly Ala Ser Lys Thr Ser Ser Arg Arg Ser Ser Met Ser Ala
            420                 425                 430 gaa gaa acg gag cat gcg tgt tag                                      1320
Glu Glu Thr Glu His Ala Cys
        435
```

<210> SEQ ID NO 13
<211> LENGTH: 434
<212> TYPE: PRT
<213> ORGANISM: Artificial
<220> FEATURE:
<223> OTHER INFORMATION: Description of Artificial Sequence: fused
      protein composed of HisTag-PTD-MITF wh mutant

<400> SEQUENCE: 13

Met Gly Gly Ser His His His His His His Gly Gly Tyr Gly Arg Lys
1               5                   10                  15

Lys Arg Arg Gln Arg Arg Arg Gly Met Leu Glu Tyr Ser His Tyr Gln
            20                  25                  30

Val Gln Thr His Leu Glu Asn Pro Thr Lys Tyr His Ile Gln Gln Ala
        35                  40                  45

Gln Arg His Gln Val Lys Gln Tyr Leu Ser Thr Thr Leu Ala Asn Lys 50                  55                  60
His Ala Ser Gln Val Leu Ser Ser Pro Cys Pro Asn Gln Pro Gly Asp
 65                  70                  75                  80

His Ala Met Pro Pro Val Pro Gly Ser Ser Ala Pro Asn Ser Pro Met
                 85                  90                  95

Ala Met Leu Thr Leu Asn Ser Asn Cys Glu Lys Glu Ala Phe Tyr Lys
            100                 105                 110

Phe Glu Glu Gln Ser Arg Ala Glu Ser Glu Cys Pro Gly Met Asn Thr
        115                 120                 125

His Ser Arg Ala Ser Cys Met Gln Met Asp Asp Val Ile Asp Asp Ile
130                 135                 140

Ile Ser Leu Glu Ser Ser Tyr Asn Glu Glu Ile Leu Gly Leu Met Asp
145                 150                 155                 160

Pro Ala Leu Gln Met Ala Asn Thr Leu Pro Val Ser Gly Asn Leu Ile
                165                 170                 175

Asp Leu Tyr Ser Asn Gln Gly Leu Pro Pro Gly Leu Thr Ile Ser
            180                 185                 190

Asn Ser Cys Pro Ala Asn Leu Pro Asn Ile Lys Arg Glu Leu Thr Glu
        195                 200                 205

Ser Glu Ala Arg Ala Leu Ala Lys Glu Arg Gln Lys Lys Asp Asn His
    210                 215                 220

Asn Leu Asn Glu Arg Arg Arg Phe Asn Ile Asn Asp Arg Ile Lys
225                 230                 235                 240

Glu Leu Gly Thr Leu Ile Pro Lys Ser Asn Asp Pro Asp Met Arg Trp
                245                 250                 255

Asn Lys Gly Thr Ile Leu Lys Ala Ser Val Asp Tyr Ile Arg Lys Leu
            260                 265                 270

Gln Arg Glu Gln Gln Arg Ala Lys Asp Leu Glu Asn Arg Gln Lys Lys
        275                 280                 285

Leu Glu His Ala Asn Arg His Leu Leu Leu Arg Val Gln Glu Leu Glu
    290                 295                 300

Met Gln Ala Arg Ala His Gly Leu Ser Leu Ile Pro Ser Thr Gly Leu
305                 310                 315                 320

Cys Ser Pro Asp Leu Val Asn Arg Ile Ile Lys Gln Glu Pro Val Leu
                325                 330                 335

Glu Asn Cys Ser Gln Glu Leu Val Gln His Gln Ala Asp Leu Thr Cys
            340                 345                 350

Thr Thr Thr Leu Asp Leu Thr Asp Gly Thr Ile Thr Phe Thr Asn Asn
        355                 360                 365

Leu Gly Thr Met Pro Glu Ser Ser Pro Ala Tyr Ser Ile Pro Arg Lys
    370                 375                 380

Met Gly Ser Asn Leu Glu Asp Ile Leu Met Asp Asp Ala Leu Ser Pro
385                 390                 395                 400

Val Gly Val Thr Asp Pro Leu Leu Ser Ser Val Ser Pro Gly Ala Ser
                405                 410                 415

Lys Thr Ser Ser Arg Arg Ser Ser Met Ser Ala Glu Glu Thr Glu His
            420                 425                 430

Ala Cys

<210> SEQ ID NO 14
<211> LENGTH: 1305
<212> TYPE: DNA
<213> ORGANISM: Artificial
<220> FEATURE:

<223> OTHER INFORMATION: Description of Artificial Sequence: DNA coding
      the fused protein composed of HisTag-PTD-MITF wh mutant
<220> FEATURE:
<221> NAME/KEY: CDS
<222> LOCATION: (1)..(1305)

<400> SEQUENCE: 14

| | | | | | | | | | | | | | | | | |
|---|---|---|---|---|---|---|---|---|---|---|---|---|---|---|---|---|
| atg | ggg | ggt | tct | cat | cat | cat | cat | cat | cat | ggt | ggt | tat | ggc | agg | aag | 48 |
| Met | Gly | Gly | Ser | His | His | His | His | His | His | Gly | Gly | Tyr | Gly | Arg | Lys | |
| 1 | | | 5 | | | | | 10 | | | | | | 15 | | |
| aag | cgg | aga | cag | cga | cga | aga | ggt | atg | cta | gaa | tac | agt | cac | tac | cag | 96 |
| Lys | Arg | Arg | Gln | Arg | Arg | Arg | Gly | Met | Leu | Glu | Tyr | Ser | His | Tyr | Gln | |
| | | 20 | | | | | 25 | | | | | 30 | | | | |
| gtg | cag | acc | cac | ctg | gaa | aac | ccc | acc | aag | tac | cac | ata | cag | caa | gct | 144 |
| Val | Gln | Thr | His | Leu | Glu | Asn | Pro | Thr | Lys | Tyr | His | Ile | Gln | Gln | Ala | |
| | 35 | | | | | 40 | | | | | 45 | | | | | |
| cag | agg | cac | cag | gta | aag | cag | tac | ctt | tct | acc | act | tta | gca | aat | aaa | 192 |
| Gln | Arg | His | Gln | Val | Lys | Gln | Tyr | Leu | Ser | Thr | Thr | Leu | Ala | Asn | Lys | |
| 50 | | | | | 55 | | | | | 60 | | | | | | |
| cat | gcc | agc | caa | gtc | ctg | agc | tca | cca | tgt | cca | aac | cag | cct | ggc | gac | 240 |
| His | Ala | Ser | Gln | Val | Leu | Ser | Ser | Pro | Cys | Pro | Asn | Gln | Pro | Gly | Asp | |
| 65 | | | | 70 | | | | | 75 | | | | | 80 | | |
| cat | gcc | atg | cca | cca | gtg | ccg | ggg | agc | agc | gca | ccc | aac | agc | cct | atg | 288 |
| His | Ala | Met | Pro | Pro | Val | Pro | Gly | Ser | Ser | Ala | Pro | Asn | Ser | Pro | Met | |
| | | | 85 | | | | | 90 | | | | | 95 | | | |
| gct | atg | ctc | act | ctt | aac | tcc | aac | tgt | gaa | aaa | gag | gca | ttt | tat | aag | 336 |
| Ala | Met | Leu | Thr | Leu | Asn | Ser | Asn | Cys | Glu | Lys | Glu | Ala | Phe | Tyr | Lys | |
| | | 100 | | | | | 105 | | | | | 110 | | | | |
| ttt | gag | gag | cag | agc | agg | gca | gag | agt | gag | tgc | cca | ggt | atg | aac | acg | 384 |
| Phe | Glu | Glu | Gln | Ser | Arg | Ala | Glu | Ser | Glu | Cys | Pro | Gly | Met | Asn | Thr | |
| 115 | | | | | 120 | | | | | 125 | | | | | | |
| cac | tct | cga | gcg | tcg | tgc | atg | cag | atg | gat | gat | gta | att | gat | gac | atc | 432 |
| His | Ser | Arg | Ala | Ser | Cys | Met | Gln | Met | Asp | Asp | Val | Ile | Asp | Asp | Ile | |
| | 130 | | | | | 135 | | | | | 140 | | | | | |
| atc | agc | ctg | gaa | tca | agt | tat | aat | gaa | gaa | att | ttg | ggc | ttg | atg | gat | 480 |
| Ile | Ser | Leu | Glu | Ser | Ser | Tyr | Asn | Glu | Glu | Ile | Leu | Gly | Leu | Met | Asp | |
| 145 | | | | 150 | | | | | 155 | | | | | 160 | | |
| ccg | gcc | ttg | caa | atg | gca | aat | acg | tta | ccc | gtc | tct | gga | aac | ttg | atc | 528 |
| Pro | Ala | Leu | Gln | Met | Ala | Asn | Thr | Leu | Pro | Val | Ser | Gly | Asn | Leu | Ile | |
| | | | 165 | | | | | 170 | | | | | 175 | | | |
| gac | ctc | tac | agc | aac | cag | ggc | ctg | cca | ccg | cca | ggc | ctt | acc | atc | agc | 576 |
| Asp | Leu | Tyr | Ser | Asn | Gln | Gly | Leu | Pro | Pro | Pro | Gly | Leu | Thr | Ile | Ser | |
| | | 180 | | | | | 185 | | | | | 190 | | | | |
| aac | tcc | tgt | cca | gcc | aac | ctt | ccc | aac | ata | aaa | agg | gag | ctc | aca | gag | 624 |
| Asn | Ser | Cys | Pro | Ala | Asn | Leu | Pro | Asn | Ile | Lys | Arg | Glu | Leu | Thr | Glu | |
| | 195 | | | | | 200 | | | | | 205 | | | | | |
| tct | gaa | gca | aga | gca | ttg | gct | aaa | gag | agg | cag | aaa | aag | gac | aat | cac | 672 |
| Ser | Glu | Ala | Arg | Ala | Leu | Ala | Lys | Glu | Arg | Gln | Lys | Lys | Asp | Asn | His | |
| 210 | | | | | 215 | | | | | 220 | | | | | | |
| aac | ttg | aat | gaa | cga | aga | aga | aga | ttt | aac | ata | aac | gac | cgc | att | aag | 720 |
| Asn | Leu | Asn | Glu | Arg | Arg | Arg | Arg | Phe | Asn | Ile | Asn | Asp | Arg | Ile | Lys | |
| 225 | | | | 230 | | | | | 235 | | | | | 240 | | |
| gag | cta | ggt | act | ctg | atc | ccc | aag | tca | aat | gat | cca | gac | atg | cgg | tgg | 768 |
| Glu | Leu | Gly | Thr | Leu | Ile | Pro | Lys | Ser | Asn | Asp | Pro | Asp | Met | Arg | Trp | |
| | | | 245 | | | | | 250 | | | | | 255 | | | |
| aac | aag | gga | acc | att | ctc | aag | gcc | tct | gtg | gac | tac | atc | cgg | aag | ttg | 816 |
| Asn | Lys | Gly | Thr | Ile | Leu | Lys | Ala | Ser | Val | Asp | Tyr | Ile | Arg | Lys | Leu | |
| | | 260 | | | | | 265 | | | | | 270 | | | | |
| caa | cgg | gaa | cag | caa | cga | gct | aag | gac | ctt | gaa | aac | cga | cag | aag | aag | 864 |
| Gln | Arg | Glu | Gln | Gln | Arg | Ala | Lys | Asp | Leu | Glu | Asn | Arg | Gln | Lys | Lys | |
| | 275 | | | | | 280 | | | | | 285 | | | | | |

-continued

```
ctg gag cat gcg aac cgg cac ctg ctg ctc aga gta cag gag ctg gag      912
Leu Glu His Ala Asn Arg His Leu Leu Leu Arg Val Gln Glu Leu Glu
    290                 295                 300 atg cag gct aga gcg cat gga ctt tcc ctt atc cca tcc acc ggt ctc      960
Met Gln Ala Arg Ala His Gly Leu Ser Leu Ile Pro Ser Thr Gly Leu
305                 310                 315                 320 tgc tcg cct gat ctg gtg aat cgg atc atc aag caa gaa cca gtt ctt     1008
Cys Ser Pro Asp Leu Val Asn Arg Ile Ile Lys Gln Glu Pro Val Leu
                325                 330                 335 gag aac tgc agc cag gaa ctt gta cag cac cag gca gac ctg aca tgt     1056
Glu Asn Cys Ser Gln Glu Leu Val Gln His Gln Ala Asp Leu Thr Cys
            340                 345                 350 acg aca act ctg gat ctc acg gac ggt acc atc acc ttt acc aac aac     1104
Thr Thr Thr Leu Asp Leu Thr Asp Gly Thr Ile Thr Phe Thr Asn Asn
        355                 360                 365 ctc ggc acc atg ccg gag agc agc ccg gcc tac agc atc ccc agg aag     1152
Leu Gly Thr Met Pro Glu Ser Ser Pro Ala Tyr Ser Ile Pro Arg Lys
    370                 375                 380 atg ggc tcc aac ttg gaa gac atc ctg atg gac gat gcc ctc tca cct     1200
Met Gly Ser Asn Leu Glu Asp Ile Leu Met Asp Asp Ala Leu Ser Pro
385                 390                 395                 400 gtt gga gtc acc gac cca ctg ctg tca tca gtg tcg cca gga gct tca     1248
Val Gly Val Thr Asp Pro Leu Leu Ser Ser Val Ser Pro Gly Ala Ser
                405                 410                 415 aaa aca agc agc cgg agg agc agt atg agc gca gaa gaa acg gag cat     1296
Lys Thr Ser Ser Arg Arg Ser Ser Met Ser Ala Glu Glu Thr Glu His
            420                 425                 430 gcg tgt tag                                                         1305
Ala Cys
```

<210> SEQ ID NO 15
<211> LENGTH: 115
<212> TYPE: PRT
<213> ORGANISM: Artificial
<220> FEATURE:
<223> OTHER INFORMATION: Description of Artificial Sequence: fused
      protein composed of HisTag-PTD-MITF bHLH-Zip fragment

<400> SEQUENCE: 15

```
Met Gly Gly Ser His His His His His Gly Gly Tyr Gly Arg Lys
1               5                   10                  15

Lys Arg Arg Gln Arg Arg Gly Met Leu Ala Lys Glu Arg Gln Lys
            20                  25                  30

Lys Asp Asn His Asn Leu Ile Glu Arg Arg Arg Phe Asn Ile Asn
        35                  40                  45

Asp Arg Ile Lys Glu Leu Gly Thr Leu Ile Pro Lys Ser Asn Asp Pro
50                  55                  60

Asp Met Arg Trp Asn Lys Gly Thr Ile Leu Lys Ala Ser Val Asp Tyr
65                  70                  75                  80

Ile Arg Lys Leu Gln Arg Glu Gln Gln Arg Ala Lys Asp Leu Glu Asn
                85                  90                  95

Arg Gln Lys Lys Leu Glu His Ala Asn Arg His Leu Leu Leu Arg Val
            100                 105                 110

Gln Glu Leu
        115
```

<210> SEQ ID NO 16
<211> LENGTH: 348
<212> TYPE: DNA

<213> ORGANISM: Artificial
<220> FEATURE:
<223> OTHER INFORMATION: Description of Artificial Sequence: DNA coding the fused protein composed of HisTag-PTD-MITF bHLH-Zip protein
<220> FEATURE:
<221> NAME/KEY: CDS
<222> LOCATION: (1)..(348)

<400> SEQUENCE: 16

| atg | ggg | ggt | tct | cat | cat | cat | cat | cat | cat | ggt | ggt | tat | ggc | agg | aag | 48 |
| Met | Gly | Gly | Ser | His | His | His | His | His | His | Gly | Gly | Tyr | Gly | Arg | Lys | |
| 1 | | | | 5 | | | | | 10 | | | | | 15 | | |

| aag | cgg | aga | cag | cga | cga | aga | ggt | atg | ttg | gct | aaa | gag | agg | cag | aaa | 96 |
| Lys | Arg | Arg | Gln | Arg | Arg | Arg | Gly | Met | Leu | Ala | Lys | Glu | Arg | Gln | Lys | |
| | | | 20 | | | | | 25 | | | | | 30 | | | |

| aag | gac | aat | cac | aac | ttg | att | gaa | cga | aga | aga | ttt | aac | ata | aac | 144 |
| Lys | Asp | Asn | His | Asn | Leu | Ile | Glu | Arg | Arg | Arg | Phe | Asn | Ile | Asn | |
| | | | 35 | | | | 40 | | | | | 45 | | | |

| gac | cgc | att | aag | gag | cta | ggt | act | ctg | atc | ccc | aag | tca | aat | gat | cca | 192 |
| Asp | Arg | Ile | Lys | Glu | Leu | Gly | Thr | Leu | Ile | Pro | Lys | Ser | Asn | Asp | Pro | |
| | 50 | | | | | 55 | | | | | 60 | | | | | |

| gac | atg | cgg | tgg | aac | aag | gga | acc | att | ctc | aag | gcc | tct | gtg | gac | tac | 240 |
| Asp | Met | Arg | Trp | Asn | Lys | Gly | Thr | Ile | Leu | Lys | Ala | Ser | Val | Asp | Tyr | |
| 65 | | | | 70 | | | | | 75 | | | | | 80 | | |

| atc | cgg | aag | ttg | caa | cgg | gaa | cag | caa | cga | gct | aag | gac | ctt | gaa | aac | 288 |
| Ile | Arg | Lys | Leu | Gln | Arg | Glu | Gln | Gln | Arg | Ala | Lys | Asp | Leu | Glu | Asn | |
| | | | 85 | | | | | 90 | | | | | 95 | | | |

| cga | cag | aag | aag | ctg | gag | cat | gcg | aac | cgg | cac | ctg | ctc | ctc | aga | gta | 336 |
| Arg | Gln | Lys | Lys | Leu | Glu | His | Ala | Asn | Arg | His | Leu | Leu | Leu | Arg | Val | |
| | | 100 | | | | | 105 | | | | | 110 | | | | |

| cag | gag | ctg | tag | 348 |
| Gln | Glu | Leu | | |
| | | 115 | | |

<210> SEQ ID NO 17
<211> LENGTH: 35
<212> TYPE: DNA
<213> ORGANISM: Artificial
<220> FEATURE:
<223> OTHER INFORMATION: Description of Artificial Sequence: primer M-tat

<400> SEQUENCE: 17
gcgacgaaga ggtatgctag aatacagtca ctacc                35

<210> SEQ ID NO 18
<211> LENGTH: 36
<212> TYPE: DNA
<213> ORGANISM: Artificial
<220> FEATURE:
<223> OTHER INFORMATION: Description of Artificial Sequence: primer tat 3

<400> SEQUENCE: 18
ggcaggaaga agcggagaca gcgacgaaga ggtatg                36

<210> SEQ ID NO 19
<211> LENGTH: 35
<212> TYPE: DNA
<213> ORGANISM: Artificial
<220> FEATURE:
<223> OTHER INFORMATION: Description of Artificial Sequence: primer tat 2

<400> SEQUENCE: 19

```
atcatcatca tggtggttat ggcaggaaga agcgg                              35
```

<210> SEQ ID NO 20
<211> LENGTH: 40
<212> TYPE: DNA
<213> ORGANISM: Artificial
<220> FEATURE:
<223> OTHER INFORMATION: Description of Artificial Sequence: primer
      tat 1

<400> SEQUENCE: 20

```
taaaccatgg ggggttctca tcatcatcat catcatggtg                         40
```

<210> SEQ ID NO 21
<211> LENGTH: 305
<212> TYPE: PRT
<213> ORGANISM: Artificial
<220> FEATURE:
<223> OTHER INFORMATION: Description of Artificial Sequence: MITF A-type
      N-terminal region (1-305)

<400> SEQUENCE: 21

| Met | Gln | Ser | Glu | Ser | Gly | Ile | Val | Ala | Asp | Phe | Glu | Val | Gly | Glu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Phe His Glu Glu Pro Lys Thr Tyr Tyr Glu Leu Lys Ser Gln Pro Leu
             20                  25                  30

Lys Ser Ser Ser Ala Glu His Ser Gly Ala Ser Lys Pro Pro Leu
         35                  40                  45

Ser Ser Ser Thr Met Thr Ser Arg Ile Leu Leu Arg Gln Gln Leu Met
50                  55                  60

Arg Glu Gln Met Gln Glu Gln Glu Arg Arg Glu Gln Gln Gln Lys Leu
65                  70                  75                  80

Gln Ala Ala Gln Phe Met Gln Arg Val Ala Val Ser Gln Thr Pro
             85                  90                  95

Ala Ile Asn Val Ser Val Pro Thr Thr Leu Pro Ser Ala Thr Gln Val
                 100                 105                 110

Pro Met Glu Val Leu Lys Val Gln Thr His Leu Glu Asn Pro Thr Lys
             115                 120                 125

Tyr His Ile Gln Gln Ala Gln Arg His Gln Val Lys Gln Tyr Leu Ser
         130                 135                 140

Thr Thr Leu Ala Asn Lys His Ala Ser Gln Val Leu Ser Ser Pro Cys
145                 150                 155                 160

Pro Asn Gln Pro Gly Asp His Ala Met Pro Pro Val Pro Gly Ser Ser
                 165                 170                 175

Ala Pro Asn Ser Pro Met Ala Met Leu Thr Leu Asn Ser Asn Cys Glu
             180                 185                 190

Lys Glu Ala Phe Tyr Lys Phe Glu Glu Gln Ser Arg Ala Glu Ser Glu
         195                 200                 205

Cys Pro Gly Met Asn Thr His Ser Arg Ala Ser Cys Met Gln Met Asp
     210                 215                 220

Asp Val Ile Asp Asp Ile Ile Ser Leu Glu Ser Ser Tyr Asn Glu Glu
225                 230                 235                 240

Ile Leu Gly Leu Met Asp Pro Ala Leu Gln Met Ala Asn Thr Leu Pro
             245                 250                 255

Val Ser Gly Asn Leu Ile Asp Leu Tyr Ser Asn Gln Gly Leu Pro Pro
                 260                 265                 270

Pro Gly Leu Thr Ile Ser Asn Ser Cys Pro Ala Asn Leu Pro Asn Ile
         275                 280                 285

```
Lys Arg Glu Leu Thr Ala Cys Ile Phe Pro Thr Glu Ser Glu Ala Arg
    290                 295                 300

Ala
305

<210> SEQ ID NO 22
<211> LENGTH: 918
<212> TYPE: DNA
<213> ORGANISM: Artificial
<220> FEATURE:
<223> OTHER INFORMATION: Description of Artificial Sequence: DNA coding
      MITF A-type N-terminal region (1-305)
<220> FEATURE:
<221> NAME/KEY: CDS
<222> LOCATION: (1)..(918)

<400> SEQUENCE: 22 atg cag tcc gaa tcg gga atc gtg gcg gat ttc gaa gtc ggg gag gag      48
Met Gln Ser Glu Ser Gly Ile Val Ala Asp Phe Glu Val Gly Glu Glu
1               5                   10                  15 ttt cac gaa gaa ccc aaa acc tat tac gaa ctc aaa agt caa cct ctg      96
Phe His Glu Glu Pro Lys Thr Tyr Tyr Glu Leu Lys Ser Gln Pro Leu
            20                  25                  30 aag agc agc agt tct gca gag cat tct ggg gcc tcc aag cct ccg tta     144
Lys Ser Ser Ser Ser Ala Glu His Ser Gly Ala Ser Lys Pro Pro Leu
        35                  40                  45 agc tcc tcc act atg aca tca cgc atc ttg cta cgc cag caa ctc atg     192
Ser Ser Ser Thr Met Thr Ser Arg Ile Leu Leu Arg Gln Gln Leu Met
    50                  55                  60 cgt gag cag atg cag gag cag gag cgc agg gag cag cag cag aag ctg     240
Arg Glu Gln Met Gln Glu Gln Glu Arg Arg Glu Gln Gln Gln Lys Leu
65                  70                  75                  80 cag gca gcc cag ttc atg caa cag aga gtg gcc gtg agt cag aca cca     288
Gln Ala Ala Gln Phe Met Gln Gln Arg Val Ala Val Ser Gln Thr Pro
                85                  90                  95 gcc ata aac gtc agc gtg ccc acc acc ctt ccc tct gcc acc cag gtg     336
Ala Ile Asn Val Ser Val Pro Thr Thr Leu Pro Ser Ala Thr Gln Val
            100                 105                 110 ccg atg gaa gtc ctt aag gtg cag acc cac ctg gaa aac ccc acc aag     384
Pro Met Glu Val Leu Lys Val Gln Thr His Leu Glu Asn Pro Thr Lys
        115                 120                 125 tac cac ata cag caa gct cag agg cac cag gta aag cag tac ctt tct     432
Tyr His Ile Gln Gln Ala Gln Arg His Gln Val Lys Gln Tyr Leu Ser
    130                 135                 140 acc act tta gca aat aaa cat gcc agc caa gtc ctg agc tca cca tgt     480
Thr Thr Leu Ala Asn Lys His Ala Ser Gln Val Leu Ser Ser Pro Cys
145                 150                 155                 160 cca aac cag cct ggc gac cat gcc atg cca cca gtg ccg ggg agc agc     528
Pro Asn Gln Pro Gly Asp His Ala Met Pro Pro Val Pro Gly Ser Ser
                165                 170                 175 gca ccc aac agc cct atg gct atg ctc act ctt aac tcc aac tgt gaa     576
Ala Pro Asn Ser Pro Met Ala Met Leu Thr Leu Asn Ser Asn Cys Glu
            180                 185                 190 aaa gag gca ttt tat aag ttt gag gag cag agc agg gca gag agt gag     624
Lys Glu Ala Phe Tyr Lys Phe Glu Glu Gln Ser Arg Ala Glu Ser Glu
        195                 200                 205 tgc cca ggt atg aac acg cac tct cga gcg tcg tgc atg cag atg gat     672
Cys Pro Gly Met Asn Thr His Ser Arg Ala Ser Cys Met Gln Met Asp
    210                 215                 220 gat gta att gat gac atc atc agc ctg gaa tca agt tat aat gaa gaa     720
Asp Val Ile Asp Asp Ile Ile Ser Leu Glu Ser Ser Tyr Asn Glu Glu
```

```
                225                 230                 235                 240
att ttg ggc ttg atg gat ccg gcc ttg caa atg gca aat acg tta ccc       768
Ile Leu Gly Leu Met Asp Pro Ala Leu Gln Met Ala Asn Thr Leu Pro
                245                 250                 255 gtc tct gga aac ttg atc gac ctc tac agc aac cag ggc ctg cca ccg       816
Val Ser Gly Asn Leu Ile Asp Leu Tyr Ser Asn Gln Gly Leu Pro Pro
        260                 265                 270 cca ggc ctt acc atc agc aac tcc tgt cca gcc aac ctt ccc aac ata       864
Pro Gly Leu Thr Ile Ser Asn Ser Cys Pro Ala Asn Leu Pro Asn Ile
            275                 280                 285 aaa agg gag ctc aca gcg tgt att ttc ccc aca gag tct gaa gca aga       912
Lys Arg Glu Leu Thr Ala Cys Ile Phe Pro Thr Glu Ser Glu Ala Arg
        290                 295                 300 gca tga                                                               918
Ala
305
```

<210> SEQ ID NO 23
<211> LENGTH: 329
<212> TYPE: PRT
<213> ORGANISM: Artificial
<220> FEATURE:
<223> OTHER INFORMATION: Description of Artificial Sequence: fused
    protein composed of HitTag-PTD-MITF A-type N-terminal region
    (1-305)

<400> SEQUENCE: 23

```
Met Gly Gly Ser His His His His His His Gly Gly Tyr Gly Arg Lys
1               5                   10                  15

Lys Arg Arg Gln Arg Arg Gly Met Gln Ser Glu Ser Gly Ile Val
            20                  25                  30

Ala Asp Phe Glu Val Gly Glu Glu Phe His Glu Glu Pro Lys Thr Tyr
        35                  40                  45

Tyr Glu Leu Lys Ser Gln Pro Leu Lys Ser Ser Ser Ala Glu His
    50                  55                  60

Ser Gly Ala Ser Lys Pro Pro Leu Ser Ser Thr Met Thr Ser Arg
65                  70                  75                  80

Ile Leu Leu Arg Gln Gln Leu Met Arg Glu Gln Met Gln Glu Gln Glu
            85                  90                  95

Arg Arg Glu Gln Gln Gln Lys Leu Gln Ala Ala Gln Phe Met Gln Gln
            100                 105                 110

Arg Val Ala Val Ser Gln Thr Pro Ala Ile Asn Val Ser Val Pro Thr
        115                 120                 125

Thr Leu Pro Ser Ala Thr Gln Val Pro Met Glu Val Leu Lys Val Gln
    130                 135                 140

Thr His Leu Glu Asn Pro Thr Lys Tyr His Ile Gln Gln Ala Gln Arg
145                 150                 155                 160

His Gln Val Lys Gln Tyr Leu Ser Thr Thr Leu Ala Asn Lys His Ala
            165                 170                 175

Ser Gln Val Leu Ser Ser Pro Cys Pro Asn Gln Pro Gly Asp His Ala
        180                 185                 190

Met Pro Pro Val Pro Gly Ser Ser Ala Pro Asn Ser Pro Met Ala Met
    195                 200                 205

Leu Thr Leu Asn Ser Asn Cys Glu Lys Glu Ala Phe Tyr Lys Phe Glu
    210                 215                 220

Glu Gln Ser Arg Ala Glu Ser Glu Cys Pro Gly Met Asn Thr His Ser
225                 230                 235                 240
```

```
Arg Ala Ser Cys Met Gln Met Asp Asp Val Ile Asp Asp Ile Ile Ser
                245                 250                 255

Leu Glu Ser Ser Tyr Asn Glu Glu Ile Leu Gly Leu Met Asp Pro Ala
                260                 265                 270

Leu Gln Met Ala Asn Thr Leu Pro Val Ser Gly Asn Leu Ile Asp Leu
            275                 280                 285

Tyr Ser Asn Gln Gly Leu Pro Pro Gly Leu Thr Ile Ser Asn Ser
        290                 295                 300

Cys Pro Ala Asn Leu Pro Asn Ile Lys Arg Glu Leu Thr Ala Cys Ile
305                 310                 315                 320

Phe Pro Thr Glu Ser Glu Ala Arg Ala
                325

<210> SEQ ID NO 24
<211> LENGTH: 990
<212> TYPE: DNA
<213> ORGANISM: Artificial
<220> FEATURE:
<223> OTHER INFORMATION: Description of Artificial Sequence: DNA coding
      the fused protein composed of HisTag-PTD-MITF A-type N-terminal
      region (1-305)
<220> FEATURE:
<221> NAME/KEY: CDS
<222> LOCATION: (1)..(990)

<400> SEQUENCE: 24 atg ggg ggt tct cat cat cat cat cat cat ggt ggt tat ggc agg aag      48
Met Gly Gly Ser His His His His His His Gly Gly Tyr Gly Arg Lys
1               5                   10                  15 aag cgg aga cag cga cga aga ggt atg cag tcc gaa tcg gga atc gtg      96
Lys Arg Arg Gln Arg Arg Arg Gly Met Gln Ser Glu Ser Gly Ile Val
            20                  25                  30 gcg gat ttc gaa gtc ggg gag gag ttt cac gaa gaa ccc aaa acc tat     144
Ala Asp Phe Glu Val Gly Glu Glu Phe His Glu Glu Pro Lys Thr Tyr
        35                  40                  45 tac gaa ctc aaa agt caa cct ctg aag agc agc agt tct gca gag cat     192
Tyr Glu Leu Lys Ser Gln Pro Leu Lys Ser Ser Ser Ser Ala Glu His
    50                  55                  60 tct ggg gcc tcc aag cct ccg tta agc tcc tcc act atg aca tca cgc     240
Ser Gly Ala Ser Lys Pro Pro Leu Ser Ser Ser Thr Met Thr Ser Arg
65                  70                  75                  80 atc ttg cta cgc cag caa ctc atg cgt gag cag atg cag gag cag gag     288
Ile Leu Leu Arg Gln Gln Leu Met Arg Glu Gln Met Gln Glu Gln Glu
                85                  90                  95 cgc agg gag cag cag cag aag ctg cag gca gcc cag ttc atg caa cag     336
Arg Arg Glu Gln Gln Gln Lys Leu Gln Ala Ala Gln Phe Met Gln Gln
            100                 105                 110 aga gtg gcc gtg agt cag aca cca gcc ata aac gtc agc gtg ccc acc     384
Arg Val Ala Val Ser Gln Thr Pro Ala Ile Asn Val Ser Val Pro Thr
        115                 120                 125 acc ctt ccc tct gcc acc cag gtg ccg atg gaa gtc ctt aag gtg cag     432
Thr Leu Pro Ser Ala Thr Gln Val Pro Met Glu Val Leu Lys Val Gln
    130                 135                 140 acc cac ctg gaa aac ccc acc aag tac cac ata cag caa gct cag agg     480
Thr His Leu Glu Asn Pro Thr Lys Tyr His Ile Gln Gln Ala Gln Arg
145                 150                 155                 160 cac cag gta aag cag tac ctt tct acc act tta gca aat aaa cat gcc     528
His Gln Val Lys Gln Tyr Leu Ser Thr Thr Leu Ala Asn Lys His Ala
                165                 170                 175 agc caa gtc ctg agc tca cca tgt cca aac cag cct ggc gac cat gcc     576
Ser Gln Val Leu Ser Ser Pro Cys Pro Asn Gln Pro Gly Asp His Ala
```

-continued

```
            180                 185                 190
atg cca cca gtg ccg ggg agc agc gca ccc aac agc cct atg gct atg    624
Met Pro Pro Val Pro Gly Ser Ser Ala Pro Asn Ser Pro Met Ala Met
        195                 200                 205 ctc act ctt aac tcc aac tgt gaa aaa gag gca ttt tat aag ttt gag    672
Leu Thr Leu Asn Ser Asn Cys Glu Lys Glu Ala Phe Tyr Lys Phe Glu
    210                 215                 220 gag cag agc agg gca gag agt gag tgc cca ggt atg aac acg cac tct    720
Glu Gln Ser Arg Ala Glu Ser Glu Cys Pro Gly Met Asn Thr His Ser
225                 230                 235                 240 cga gcg tcg tgc atg cag atg gat gat gta att gat gac atc atc agc    768
Arg Ala Ser Cys Met Gln Met Asp Asp Val Ile Asp Asp Ile Ile Ser
                245                 250                 255 ctg gaa tca agt tat aat gaa gaa att ttg ggc ttg atg gat ccg gcc    816
Leu Glu Ser Ser Tyr Asn Glu Glu Ile Leu Gly Leu Met Asp Pro Ala
        260                 265                 270 ttg caa atg gca aat acg tta ccc gtc tct gga aac ttg atc gac ctc    864
Leu Gln Met Ala Asn Thr Leu Pro Val Ser Gly Asn Leu Ile Asp Leu
    275                 280                 285 tac agc aac cag ggc ctg cca ccg cca ggc ctt acc atc agc aac tcc    912
Tyr Ser Asn Gln Gly Leu Pro Pro Pro Gly Leu Thr Ile Ser Asn Ser
290                 295                 300 tgt cca gcc aac ctt ccc aac ata aaa agg gag ctc aca gcg tgt att    960
Cys Pro Ala Asn Leu Pro Asn Ile Lys Arg Glu Leu Thr Ala Cys Ile
305                 310                 315                 320 ttc ccc aca gag tct gaa gca aga gca tga                            990
Phe Pro Thr Glu Ser Glu Ala Arg Ala
                325

<210> SEQ ID NO 25
<211> LENGTH: 31
<212> TYPE: DNA
<213> ORGANISM: Artificial
<220> FEATURE:
<223> OTHER INFORMATION: Description of Artificial Sequence: primer
      HLH F

<400> SEQUENCE: 25
gagacgaaga ggtatgttgg ctaaagagag g                                 31

<210> SEQ ID NO 26
<211> LENGTH: 30
<212> TYPE: DNA
<213> ORGANISM: Artificial
<220> FEATURE:
<223> OTHER INFORMATION: Description of Artificial Sequence: primer
      pTD3-MITFa

<400> SEQUENCE: 26
cgccgcggaa tgcagtccga atcgggaatc                                   30

<210> SEQ ID NO 27
<211> LENGTH: 35
<212> TYPE: DNA
<213> ORGANISM: Artificial
<220> FEATURE:
<223> OTHER INFORMATION: Description of Artificial Sequence: primer
      MITFR-N

<400> SEQUENCE: 27
gaattcacta tgctcttgct tcagactctg tgggg                             35

<210> SEQ ID NO 28
```

```
                                  -continued
<211> LENGTH: 75
<212> TYPE: DNA
<213> ORGANISM: Artificial
<220> FEATURE:
<223> OTHER INFORMATION: Description of Artificial Sequence: DNA coding
      for fused proteins comprised of HisTag-linker-PTD-linker-MITF
<220> FEATURE:
<221> NAME/KEY: CDS
<222> LOCATION: (1)..(75)

<400> SEQUENCE: 28 atg ggg ggt tct cat cat cat cat cat cat ggt ggt tat ggc agg aag        48
Met Gly Gly Ser His His His His His His Gly Gly Tyr Gly Arg Lys
1               5                   10                  15 aag cgg aga cag cga cga aga ggt atg                                    75
Lys Arg Arg Gln Arg Arg Arg Gly Met
            20                  25

<210> SEQ ID NO 29
<211> LENGTH: 25
<212> TYPE: PRT
<213> ORGANISM: Artificial
<220> FEATURE:
<223> OTHER INFORMATION: Description of Artificial Sequence: DNA coding
      for fused proteins comprised of HisTag-linker-PTD-linker-MITF

<400> SEQUENCE: 29

Met Gly Gly Ser His His His His His His Gly Gly Tyr Gly Arg Lys
1               5                   10                  15

Lys Arg Arg Gln Arg Arg Arg Gly Met
            20                  25
```

CELL DEATH INDUCERS FOR MAST CELLS

CROSS-REFERENCE TO RELATED APPLICATIONS

This application is a National Stage Application of PCT/JP02/06790, filed Jul. 4, 2002, which claims priority from Japanese Patent Application No. 2001-204567, filed Jul. 5, 2001, both of which are incorporated herein by reference in their entireties.

FIELD OF THE INVENTION

The present invention relates to medical use of MITF variants. More specifically, it relates to medical use of fusion proteins having the MITF variant as a component.

BACKGROUND

MITF (an abbreviation for microphthalmia-associated transcription factor) is one of transcription regulators present in organisms; it is a protein capable of modulating an expression of a c-kit gene, which is specific to mast cells.

MITF is a known substance (Cell, vol. 74, 395404, 1993); it was, however, a gene that codes for MITF that was first discovered. That is to say, the gene was isolated as a causal gene for a mi/ml mouse. In the mi/ml mouse, because of a mutation in the MITF gene, that is, a deletion of one amino acid in the transcription activation region of the MITF gene, normal MITF is not expressed. The mi/ml mouse is a mutant mouse having hypoplasia of an eyeball, melanocyte deficiency, mast cell loss, and osteopetrosis of a bone as main symptoms thereof, and presents differentiation anomalies in tissues, such as melanocytes, mast cells, retinal pigment epithelial cells, and osteoclasts. These cell differentiation disorders in the mi/ml mouse are attributed to the fact that normal MITF is not expressed, and gene transcription is not activated by MITF.

Furthermore, in Northern-blot analyses of a tissue distribution of an expression, using tissues or cell lines from a normal mouse, it was found that MITF mRNA was expressed in the heart, in melanocytes, and in mast cells. In recent years, the existence of MITF isoforms has been reported; i.e. a melanocyte type (M type), a heart type (H type), and an A-type, in which the cDNA sequences were different at the 5' end [Seikagaku (Journal of the Japanese Biochemical Society), vol. 71, no. 1, 61–64, 1999]. The MITF gene comprises 10 (M type) or 11 (A and H types) exons, and all three types are substantially common beyond exon 2. In the M type, two further types are distinguished by an addition, or lack thereof, of exon 5b, which comprises 18 bases coding for 6 amino acids. The A and H types completely match each other beyond exon 1B, exon 1 at the 5' end being different. The A and H types and the M type are common beyond exon 2; however the M type has no exon 1B upstream of exon 2, which is linked to a specific exon 1. Furthermore, it has been shown that the promoter for each type is different from the genomic sequence.

An MITF protein is assumed to comprise a nuclear localization region, a transcription activation region, a DNA binding region, a dimerization region, and an activation region for MITF itself; the presence of these regions is common to all known types. The MITF protein is a transcription regulator, which has a bHLH-Zip (base-helix-loop-helix/leucine zipper) motif at a center of its structure, it forms a dimer to bind to DNA, and activates transcription of targeted genes. Since major differences have been reported between transcription activation capabilities of the A-type and the H type, there is assumed to be a function that regulates the transcriptional activity at exon 1, which differs in genetic sequence between the two types.

Furthermore, it has been reported that the MITF protein works as a transcription regulator in melanocytes, and that it is involved in the multiplication and differentiation of melanocytes, as well as in the melanin synthesis pathway, and the like.

It has been reported that the MITF protein also acts as a transcription regulator in mast cells, modulating the expression of the c-kit gene (a transcription factor that activates the c-kit promoter) (Blood, vol. 88, no. 4, 1225–33, 1996). The c-kit gene is expressed in hematopoietic precursor cells, mast cells, pigment cells, and germ cells and regulates the multiplication and the differentiation of these cells by the action of the Si factor. It is thought that, in mast cells, MITF protein is involved in mast cell survival maintenance by regulating the expression of c-kit gene expression.

Mast cells have long been reported to be involved in allergic diseases ["IgE, Mast Cells and the Allergic Response" (Ciba Foundation symposium) 147, John Wiley & Sons, Chichester, UK, 1989]. Furthermore, diseases other than allergic diseases in which mast cells are involved include autoimmune diseases, pulmonary fibrosis, carcinomas, mastocytosis, mastocytoma, and the like.

Meanwhile, PTD (an abbreviation for Protein Transduction Domain) is a general term for domains to penetrate the biological membrane and transfer proteins into the cells (uptake). For example, in analysis of HIV antigens by domain units, it is confirmed that a TAT-derived peptide portion serves to transfer the HIV antigen inside normal T-cells, which is one of contributing factors in cell infection (Cell, vol. 55, 1179–88, 1988). Based on such observations, there have been reports of the existence of various PTDs to work in a similar way to TAT, and of techniques whereby these PTDs are fused with various proteins for translocation into cells (Current Opinion in Molecular Therapeutics 2000, vol. 2, no. 2, 162–67, 2000).

However, there have been no reports to date of techniques related to MITF or mast cells to transfer into cells using PTD.

DISCLOSURE OF THE INVENTION

An object of the present invention is to provide a novel medical use for MITF variants.

As a result of studies undertaken by the present inventors in view of the situation described above, it was discovered that, by combining MITF variants and PTD, it is possible to induce cell death in mast cells, and thus the present invention was completed.

That is to say, one aspect of the present invention is a cell death inducer for mast cells, having a fusion protein comprising a PTD and an MITF variant as an active ingredient.

One aspect of the present invention is a preventive/therapeutic agent for diseases in which mast cells are implicated, having a fusion protein comprising the PTD and the MITF variant as the active ingredient.

One aspect of the present invention is a fusion protein wherein this fusion protein comprises a His Tag, the PTD, and the MITF variant, the MITF variant being an MITF mi variant, wh variant, HLH fragment, or A-type N-terminal region (1-305) fragment, and the PTD being a TAT-derived peptide.

One aspect of the present invention is a pharmaceutical composition comprising the fusion protein and a pharmacologically acceptable carrier.

One aspect of the present invention is a method for preparing the fusion protein, the method comprising a step of producing the fusion protein using genetic engineering techniques.

One aspect of the present invention is DNA that codes for the fusion protein.

One aspect of the present invention is a method for inducing cell death in mast cells comprising administrating an effective dose of a fusion protein comprising a PTD and an MITF variant.

One aspect of the present invention is use of a fusion protein comprising a PTD and an MITF variant for preparing an agent for inducing cell death in mast cells.

DETAILED DESCRIPTION

Figure 1:
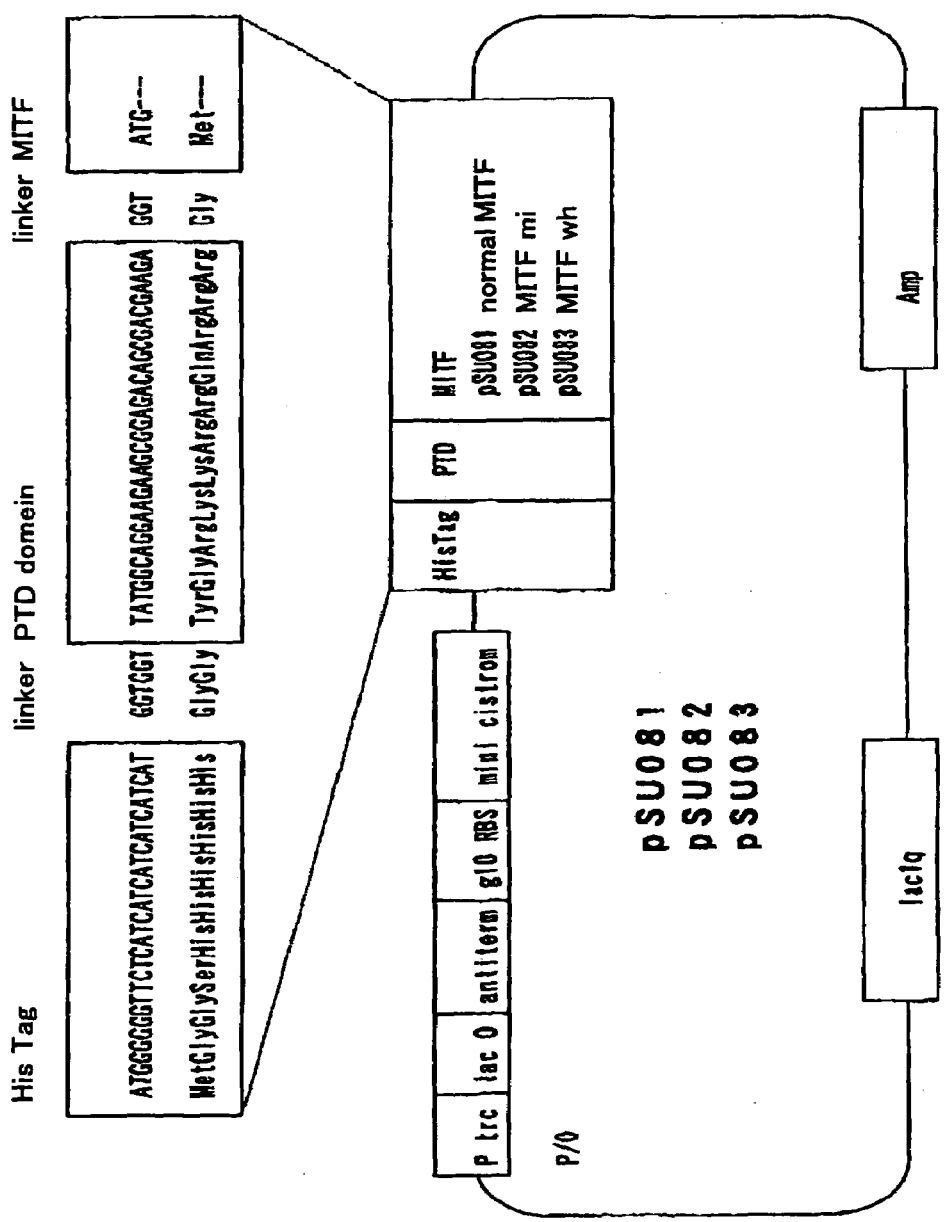
FIG. 1 schematically illustrates the structures of fusion proteins of the present invention (mi form and wh form) and plasmids pSU082 (mi form/pTrcHisB) and pSU083 (wh form/pTrcHisB) that express fusion proteins. A portion of the fusion protein SEQ ID NO. 29 and the DNA that codes for the portion of the fusion protein SEQ. ID NO. 28 are also illustrated.

Modes of embodiment for the present invention will be described in further detail hereinafter. The detailed description below is illustrative, being solely explanatory in intent, and does not limit the present invention in any way.

Furthermore, the technical and scientific terms used in the present invention, unless defined separately, have meanings that are normally understood by a person of ordinary skill in the technical field to which the present invention belongs. In the present invention, various methods known to those skilled in the art are referenced. The content of publications, and the like, which disclose such cited well-known methods, are incorporated herein by reference, as if completely set forth in their entirety in the present specification.

A. MITF Variant

The MITF variant used in the present invention is no particular restriction thereon as long as it is a natural type (wild type) MITF variant, and it has an MITF inhibitory activity. Specifically, examples thereof include the mi variant of MITF, the wh variant of MITF, and other MITF variants, for example, splicing variants (which may be derived from any of the A, H, M, or N isoforms), or a partial MITF structure having an MITF inhibitory activity, for example, a bHLH-Zip (the N-terminal residues 196 to 285 of the M isoform) fragment, an N-terminal end fragment comprising this portion, an N-terminal region of the A isoform (from the N-terminal residue 1 to 305) fragment, and the like. Specifically, examples include the MITF variant disclosed in *Trends in Genetics*, vol. 11, no. 11, 442–48, 1995; WO 00/47765; WO 01/66735 (Japanese Patent Application No. 2000-63959), and the like. Particularly preferred variants are the mi variant, the wh variant, the bHLH-Zip fragment (hereinafter, HLH fragment), and the N-terminal region (1-305) fragment of the A isoform. The relationships between the amino acid sequences thereof and base sequences are as shown in Table 1.

TABLE 1

| MITF Variant | Amino Acid Sequence | Preferable Base Sequence |
|---|---|---|
| mi variant | SEQ ID NO: 1 | SEQ ID NO: 2 |
| wh variant | SEQ ID NO: 3 | SEQ ID NO: 4 |
| HLH fragment | SEQ ID NO: 5 | SEQ ID NO: 6 |
| A-type N-terminal region | SEQ ID NO: 21 | SEQ ID NO: 22 |

Furthermore, the scope of the present invention includes structural analogs of these variants having substantially the same degree of MITF inhibitory activity as these variants. For example, these may be variants wherein one or a plurality of amino acids are substituted, deleted, inserted, or added in the above-mentioned amino acid sequences, and which have substantially the same degree of activity as these variants.

B. PTD

There is no particular restriction on the PTD used in the present invention, so long as it has the property of allowing uptake (transfer) into cells, and well-known PTDs may be used. Specifically, examples include the various oligopeptides listed in Table 2 on page 164 of the above-mentioned reference (Current Opinion in Molecular Therapeutics 2000, vol. 2, no. 2, 162–67, 2000), the various PTD oligopeptides disclosed in WO 99/10376, WO 99/29721, JP-05-505102-T, and the like.

A preferable PTD is a TAT-derived peptide (the amino acid sequence is indicated by YGRKKRRQRRR, SEQ ID NO: 7, and the preferred base sequence is indicated by SEQ ID NO: 8).

The PTD may be linked to either the N-terminal end or the terminal end of the MITF variant. Furthermore, the linkage may be either direct, or indirect via a cross-linking agent (linker). Examples of linkers include glycine residues, and the like.

C. Other Components (Domains)

The fusion protein of the present invention may be linked to a domain that has affinity to a ligand in affinity chromatography for purification. There are no particular restrictions on the domain, and well-known domains may be used. In this regard, examples include an antigen and an antibody, a receptor and a ligand, Ni—NTA (nitrilotriacetic acid) and a His Tag, avidin (or streptavidin) and biotin, and the like. A His Tag (the amino acid sequence is represented by MGGSHHHHHH, SEQ ID NO: 9, the preferred base sequence is represented by SEQ ID NO: 10) is preferred.

This domain may be linked to either the N-terminal end or the C-terminal end of the fusion protein. Furthermore, the linkage may be either direct, or indirect via a cross-linking agent (linker). Examples of linkers include glycine residues, and the like.

D. Preparation of the Fusion Protein

Examples of methods for preparing the fusion protein of the present invention include: (1) a method for synthesizing the entire fusion protein using chemical synthesis techniques; (2) a method wherein each component (domain) mentioned above is synthesized separately and then linked using chemical reaction means; and, (3) a method wherein the genes coding for each component are linked and are then all expressed as the fusion protein at one time using genetic engineering techniques, and the like. In the case of (2), methods for preparing each component include chemical synthesis methods, cell culture methods, methods using genetic engineering techniques, and the like. A PTD may also be prepared by cleavage and isolation from an HIV antigen.

A case will be described by way of example wherein the fusion protein is prepared by genetic engineering techniques.

1) DNA coding for the fusion protein is prepared. The preparation uses conventional methods. First, the gene coding for the MITF variant is prepared. The gene can be prepared by extracting mRNA from suitable cells, synthesizing cDNA using reverse transcriptase and DNA polymerase, and amplifying this with the polymerase chain reaction (PCR) method. Specifically, mRNA can be extracted using commercially available mRNA extraction kits, and the like; reverse transcription, cDNA synthesis, and amplification may be carried out by the 5'-RACE method using commercially available cDNA amplification kits, and the like (*Proc. Natl. Acad. Sci.* USA, vol. 85, 8998–9002, 1988), or by the reverse transcription polymerase chain reaction (RT-PCR) method, and the like, using suitable primers. Furthermore, the gene can also be obtained by extracting genomic DNA from a suitable cell and amplifying by PCR. Furthermore, the gene coding for MITF disclosed in well-known publications, such as the aforementioned *Cell* (1993) and WO 01/66735, may also be used. For example, the HLH fragment of the present invention may be prepared from an M-type MITF, and the N-terminal region (1-305) fragment of the A-type from an A-type MITF (MITF A/pcDNA3), respectively.

Next, a gene coding for PTD is prepared by the same method as described above and ligated to the gene coding for the MITF variant. The His Tag is prepared in the same way. Furthermore, the DNA coding for the fusion protein of the present invention can be prepared by inserting DNA coding for a fusion protein comprising a PTD-MITF variant, using a commercially available plasmid bearing the His Tag (pTrcHisB, Invitrogen).

2) An expression vector is prepared by integrating DNA into a suitable vector. The vector is used to express the fusion protein under the control of a specific promoter. This integration is performed by conventional methods.

It is possible to construct a host/vector system by purifying the target DNA obtained as described above and inserting it into vector DNA. A host combined with a replicon derived from species that is compatible with a host cell is generally used for the host/vector system. The vector DNA has an origin of replication, a promoter, a regulatory sequence (enhancer), a signal sequence, a ribosomal binding site, an RNA splicing sequence, a polyA addition site, a transcription termination sequence (terminator), and the like. Furthermore, it may have a marker sequence that allows phenotypic selection among transformed cells. Examples of the vector DNA include: vectors derived from chromosome and episome, vectors derived from bacterial plasmid, bacteriophage, vectors derived from virus such as baculovirus, papovavirus and SV40, cosmid, phagemid, and the like. Furthermore, an expression vector, a cloning vector, and the like, may be used depending on the purpose.

The promoter includes well-known promoters and can be selected according to the host for expression. For example, in cases where *Escherichia coli* is the host, examples include promoters such as a trp promoter, a lac promoter, a trc promoter (a synthetic promoter in which a −35 region of the trp promoter and a −10 region of the lac promoter are ligated), and the T7 promoter. Furthermore, the expression vector may bear a marker gene, such as $amp^r$.

Methods well known per se may be used as the method for integrating the DNA according to the present invention into the vector DNA. For example, a method may be used wherein a suitable restriction endonuclease is selected and applied to cleave the target DNA at specific sites, which is then mixed with a similarly treated vector DNA and re-linked by a ligase. Alternately, the intended recombinant vector can also be obtained by ligating a suitable linker with the target DNA and inserting this into the multicloning site of the vector that is appropriate for the purpose. Furthermore, the target protein can be prepared by using the expression vector as the vector DNA which is introduced into a host.

3) Transformants are prepared by introducing the expression vector into hosts. The transformations are performed by conventional methods. *Escherichia coli, Bacillus subtilis*, yeast, animal cells, and the like, may be used as the host. *Escherichia coli* is preferred. Furthermore, auxotrophic strains and antibiotic-sensitive strains may also be used as hosts.

Methods for preparing the transformants include methods for introducing a plasmid directly into host cells, methods for integrating the plasmid into the chromosome, and the like. The former includes the protoplast polyethylene glycol method, the electroporation method, and the like. For the latter, a portion of the DNA sequence of a gene that is present in a host chromosome may be included in a plasmid, and using a homologous sequence portion, the plasmid, or a linear fragment, is integrated into the host chromosome by homologous recombination.

4) Transformants are cultured to produce the fusion protein. Culture is performed by conventional methods, using a suitable culture medium and suitable culture conditions (temperature, time, etc.) depending on the host. In the case where *Escherichia coli* is used, in general, this is performed under culture conditions of approximately 15–43° C. (preferably 30–37° C.) and approximately 1–100 hours. Furthermore, aeration and agitation can also be added as necessary. The culturing system may be any of batch culture, semi-batch culture (fed-batch culture), or continuous culture.

5) The fusion protein produced is purified. In the case where *Escherichia coli* is used as the host, the protein is first solubilized by treatment such as sonication of cells. Purification of the fusion protein produced may be performed by techniques well known perse (WO 99/55899, and the like). Examples include methods using an Ni column, anion exchange treatments, dialysis treatments, and the like. Furthermore, use of the fusion protein of the present invention, obtained by treatment with a denaturing agent (chaotropic agent) and subsequent removal of the denaturing agent, is preferred. Examples of denaturing agents include urea, guanidine hydrochloride, thiocyanate, and the like. Conditions for adding the denaturing agent during treatment with the denaturing agent may, for example, be concentrations of approximately 1–10 M. Specifically, after treatment by contacting the fusion protein and the denaturing agent, a treatment is carried out using the Ni column in the presence of the denaturing agent; furthermore, operations to eliminate the denaturing agent are carried out by anion exchanger or dialysis treatment, so as to purify the fusion protein.

E. Characteristics of the Prepared Fusion Protein

The fusion protein of the present invention has a property of transducing into cells, in particular, into mast cells. Preferably, it comprises a His Tag, a PTD, and an MITF variant. It has a molecular weight of approximately 10–100 kilo Daltons (kDa). Preferably, it is laid out in order, from the N-terminal end, as His Tag, PTD, and MITF variant. Specific sequences are as shown in Table 2.

TABLE 2

| Fusion Protein | Amino Acid Sequence | Preferable Base Sequence |
| --- | --- | --- |
| His Tag-PTD-mi variant of MITF | SEQ ID NO: 11 | SEQ ID NO: 12 |
| His Tag-PTD-wh variant of MITF | SEQ ID NO: 13 | SEQ ID NO: 14 |
| His Tag-PTD-fragment of HLH | SEQ ID NO: 15 | SEQ ID NO: 16 |
| His Tag-PTD-A-Type N-terminal region of MITF | SEQ ID NO: 23 | SEQ ID NO: 24 |

F. Formulation

Techniques well known per se can be used to formulate the fusion protein of the present invention. For example, a pharmacologically acceptable carrier can be added to, or mixed with, the fusion protein. Examples of concentrations for the fusion protein in the pharmaceutical composition obtained by formulation include approximately 0.1–100 μg/mL or 0.1–100 nM.

G. Use Application

The MITF variant of the present invention (or, the fusion protein using the same) has such effects to inhibit the activity of endogenous MITF by translocating inside the mast cell, to inhibit the differentiation of mast cells from precursor cells, to inhibit the survival of mast cells, and to induce cell death (apoptosis) in mature mast cells. Therefore, it is anticipated that the formulation of the present invention will be useful in prevention/treatment of various diseases in which mast cells are implicated. Examples of these diseases include allergies, asthma, autoimmune diseases, pulmonary fibrosis, carcinomas, mastocytosis, mastocytoma, and the like.

H. Dosage and Administration

In terms of dosage and administration for the fusion protein of the present invention, the dosage may be selected so that the fusion protein is present at in vivo concentrations of approximately 0.001–10 μg/mL. Alternatively, for example, dosages may be of the order of 10 μg–50 mg. Administration routes include intravenous administration, subcutaneous administration, intramuscular administration, percutaneous administration, tracheobronchial administration, and the like.

EXAMPLES

Advantages, features, and possibilities for the present invention will be described hereinafter in more detail referring to illustrative examples; the present invention is not, however, limited to the following examples.

Example 1

1) Construction of the Expression Plasmid for the Fusion Protein

The expression plasmid was constructed by inserting a gene for a His Tag-PTD-MITF variant, wherein a PTD sequence is connected downstream of a His Tag for purification, downstream of which the cDNA for the MITF variant is connected, between the NcoI site, which is located upstream of the His Tag sequence, and the HindIII site in the multicloning site of the *Escherichia coli* expression vector pTrcHisB (Invitrogen, No. V360-20). See FIG. 1.

His Tag and the PTD sequences were added to the MITF cDNA by PCR. First, with the cDNA of M type MITF (pSU054, MITF-M/pT7 Blue) as the template, the upstream portion that contains MITF and the BamHI site was amplified by PCR. Furthermore, this was elongated using four kinds of primer (M-tat, Tat 3, Tat 2, and Tat 1) until the His Tag and the recognition sequence for the restriction endonuclease NcoI were added upstream of the transcription initiation codon of MITF, then cloned between the NcoI site and the BamHI site of the *Escherichia coli* expression vector pTrcHisB (this bears the lac P/O and Amp$^r$).

The primers have following base sequences.

M-tat (SEQ ID NO: 17): GCGACGAAGAGGTAT-GCTAGAATACAGTCACTACC

Tat 3 (SEQ ID NO: 18): GGCAGGMGAAGCGGAGA-CAGCGACGAAGAGGTATG

Tat 2 (SEQ ID NO: 19): ATCATCATCATGGTGGT-TATGGCAGGAAGAAGCGG

Tat 1 (SEQ ID NO: 20): TAAACCATGGGGGGTTCT-CATCATCATCATCATGGTG

Next, by digesting the M type (pSU054), the mi variant (pSU061, MITF-M mi/pT7 Blue), and the wh variant (pSU062, MITF-M/pT7 Blue) with BamHI and HindIII, respectively, a downstream portion of the MITF cDNA was isolated. The mutant portion is also contained in this portion. The isolated cDNA fragment was inserted between the BamHI site and the HindIII site of the plasmid into which the upstream portion was cloned. The pSU81 plasmid has inserted therein a fusion protein gene that contains the M type, which is the normal type MITF. pSU082 and pSU083 each have a fusion protein inserted therein, containing the mi variant and the wh variant, respectively.

2) Expression of the Fusion Protein

The constructed expression plasmid was introduced into *Escherichia coli* DH5α (Toyobo) for transformation. A volume of 50 mL of L-Broth (containing 50 μg/mL ampicillin) was inoculated with 1 platinum loop of *Escherichia coli* and cultured at 37° C. for 17 hours. Furthermore, 1 L of L-Broth (containing 50 μg/mL ampicillin and 0.2% glucose) was inoculated so as to obtain a 1% culture solution. After culturing at 37° C. until the $A_{600}$ turbidity reached approximately 0.1, IPTG (isopropyl thio-β-D-galactoside) was added so as to obtain a final concentration of 0.4 mM. After culturing for 2 hours, *Escherichia coli* was harvested.

3) Purification of the Fusion Protein

*Escherichia coli* was recovered by centrifugation, sonicated in a 20 mM HEPES buffer solution (pH 8.0; hereinafter, pH is the same) that contains 8 M urea, 0.1 M sodium chloride, and 10 mM DTT, and solubilized. The obtained lysate was applied to a Ni—NTA agarose (Qiagen) column, which is equilibrated with a 20 mM HEPES buffer solution containing 8 M urea, 0.1 M sodium chloride, 10 mM imidazole, and 1 mM DTT and washed with the same buffer solution. The protein bound to the column was eluted by the imidazole linear concentration gradient method, using the same buffer solution as the A solution and the same buffer solution, containing 200 mM imidazole, as the B solution, and analyzed by SDS-PAGE (Tefco); the fractions showing the target molecular weight were pooled.

A solution, diluted by adding both 1 volume of 20 mM HEPES buffer solution and 2 volumes of the same buffer solution containing 4 M urea to 1 volume of the eluate, was applied to a quaternary ammonium strong anion exchanger (product name: Q-Sepharose, Pharmacia), which is equilibrated with a 20 mM HEPES buffer solution containing 4 M urea and 25 mM sodium chloride, and washed with the same buffer solution. Next, after eliminating the urea by washing with a 20 mM HEPES buffer solution, the protein bound to the column was eluted with the same buffer solution containing 1 M sodium chloride. After the eluted fusion protein was dialyzed against Dulbecco's PBS (isotonic phosphate-buffered solution) containing 10% glycerol, it was dispensed and stored at −80° C.

When a final product that was obtained was analyzed by SDS-PAGE, a band showing a molecular weight of approximately 50 kilo Daltons under reducing conditions was observed. This band reacted with rabbit anti-MITF antibodies. Note that this rabbit anti-MITF antibody was obtained by affinity purification of an antiserum obtained by immunizing a rabbit with a peptide of the 20 C-terminal amino acid residues of MITF, using a column to which the same peptide was bound, to prepare antibodies that specifically recognize the same peptide.

Formulation Example 1

A composition comprising the fusion protein of the present invention and Dulbecco's PBS containing 10% glycerol was prepared.

Experimental Example 1

1) First, whether or not fusion proteins of the present invention translocate into the cells was confirmed. A fusion protein of the MITF variant prepared in Example 1 was fluorescence labeled with FITC (fluorescein-isothiocyanate) by conventional methods and added to COS7 cells. One hour after addition, a fluorescence intensity was measured using FACS (fluorescence-activated cell sorter) Calibur (Becton Dickinson). Results are shown in Table 3.

TABLE 3

| Added agent | Peak position of fluorescence intensity (FL1-H) |
|---|---|
| PBS (fusion protein is not added) | 3 |
| His Tag-PTD-mi variant of MITF | 6 |
| His Tag-PTD-wh variant of MITF | 10 |

As is apparent from Table 3, strong fluorescence is observed to be associated with the cells, confirming efficient translocation of the fusion protein into the cells.

2) Luciferase analysis was carried out to examine whether the fusion protein of the present invention translocates into cells and inhibits endogenous MITF activity.

A normal MITF expression plasmid pSU063 (MITF-M/pcDNA3), various vectors for preparing plasmids in which a luciferase gene is connected downstream of the c-kit gene promoter, that is, C-kit-Rluc expression vector pSU053 (C-kit/R-luc), and luciferase expression vector pGL2 (Lluc, Promega) were used as expression plasmids. Each plasmid was introduced (transfected) into COS7 cells. The conditions were as follows. The quantity of plasmid used was 3 µg per 6-cm dish (pSU063: pSU053: pGL2=1:1:0.1). For plasmid introduction, a transfection kit (Stratagene, #200385) was used.

A quantity of $1\times10^5$ cells per well were inoculated in a 6-well plate and left at rest for 17 hours in a $CO_2$ incubator. After adding 90 µL of distilled water and 3 µg of DNA to 10 µL of Solution 1 (a reagent included in the kit, comprising 2.5 M $CaCl_2$), an equal quantity of Solution 2 [a reagent included in the kit, comprising 2×PBS (pH 6.95)] was added and this was left stationary at room temperature for 20 minutes. The mixed DNA solution was added to the culture solution. After 24 hours, the culture medium was replaced, and 1 µg/mL of the fusion protein of the present invention (prepared in Example 1) was added.

Forty-eight hours after addition of the fusion protein of the present invention, cells were washed with PBS (−), 0.5 mL of passive lysis buffer were added per 6-well dish, and cells were collected by scraping, using a scraper. Cells were transferred to a 1.5-mL capacity tube and centrifuged at 14000 rpm at 4° C. for 5 minutes. Measurement of luciferase activity was carried out using a Dual luciferase assay kit (Promega). On a 96-well plate, 100 µL of Luciferase Assay Reagent II was added to and mixed with 20 µL of centrifugation supernatant, and firefly luciferase activity was measured. Furthermore, 100 µL of Stop & Go Reagent was further added to and mixed with the mixture, and a Renilla luciferase (R-luc) activity was measured. R-luc counts were corrected with pGL2 and then converted to a value where the R-luc on PBS addition was taken to be 1. Results are shown in Table 4.

TABLE 4

| Added agent | Luciferase activity |
|---|---|
| pSU053 + pSU063 + PBS | taken as 1 |
| pSU053 + pSU063 + mi | 0.92 |
| pSU053 + pSU063 + wh | 0.72 |

Note that, in the table, mi shows the fusion protein comprising the His Tag-PTD-MITF mi variant, and wh shows the fusion protein comprising the His Tag-PTD-MITF wh variant, respectively.

The luciferase activity expressed by the COS cells was also inhibited in the presence of the fusion protein of the present invention, suggesting that the fusion protein transfers into the cells and inhibits endogenous MITF.

Experimental Example 2

Investigation was made into how the fusion protein of the present invention influences an SCF induced mast cell differentiation system.

Bone marrow cells were prepared from normal mice; of these, $2\times10^6$/well were cultured in RPMI 1640 containing 10% FCS, 0.1 mM nonessential amino acids, 1 mM sodium pyruvate, 2 mM glutamine, 100 U/mL penicillin, 100 µg/mL streptomycin, 50 µM 2-mercaptoethanol, 2 µg/mL fusion protein of the present invention (His Tag-PTD-MITF wh variant), in the presence of 50–100 ng/mL bone marrow cell factor (SCF, IBL), in a 24-well plate. Once a week, half the quantity of the culture medium was exchanged, and in so doing, SCF was also added. After culturing at 37° C. for 21 days, a count of mast cells and a representation of c-kit and IgE receptors were measured.

The Count of mast cells was measured by a toluidine blue staining method. The toluidine blue staining was carried out according to *Current Protocols in Immunology* (Wiley) section 7.25.2, using a staining solution at pH 2.7.

The representation of c-kit was measured using FACS. Cells were suspended in 100 μL PBS containing 0.1% $NaN_3$ and 0.1% BSA, and incubated for 1 hour on ice with 5–10 μg/mL of R-PE (R-phycoerythrin)-labeled antimouse c-kit antibody (PharMingen) or R-PE-labeled rat IgG 2B, k isotype standard (PharMingen). After washing, 1 μg/mL of pyridium iodide was added, and analysis was performed with FACS Calibur (above-described). The representation of IgE receptors was measured in the same way using 5 μg/mL FITC-labeled mouse IgE and analyzed with FITC. Results for counts of mast cells are shown in Table 5.

TABLE 5

| Fusion protein of the present invention | Count of mast cells | |
| --- | --- | --- |
| | 14th day of culture | 21th day of culture |
| no addition | $9 \times 10^4$ | $3 \times 10^6$ |
| addition | $3 \times 10^4$ | $2 \times 10^5$ |

In the group to which the fusion protein of the present invention was added, at 21th day of culture, the count of mast cells decreased to no more than $1/10$, as compared to the group to which this was not added. Furthermore, results for c-kit expression at 21th day of culture are as shown in Table 6.

TABLE 6

| Fusion protein of the present invention | Peak position of fluorescence intensity |
| --- | --- |
| no addition | $1 \times 10^3$ |
| addition | $7 \times 10^1$ |

In the group to which the fusion protein of the present invention was added, at 21th day of culture, the representation of c-kit decreased to no more than $1/10$, as compared to the group to which this was not added. Furthermore, the representation of IgE receptors did not change (experimental data not shown).

Thus, it was confirmed that the fusion protein of the present invention specifically inhibits the expression of the SCF receptor c-kit in mast cell precursor cells and, as a result, strongly inhibits the differentiation of mast cells.

Experimental Example 3

The influence on mast cell survival in co-culture systems with fibroblasts was examined in order to confirm the influence of the fusion protein of the present invention on mature mast cells.

Splenic cells were prepared from normal mice, cultured in RPMI 1640 containing 10% FCS, 0.1 mM non-essential amino acids, 1 mM sodium pyruvate, 2 mM glutamine, 100 U/mL penicillin, 100 μg/mL streptomycin, and 50 μM 2-mercaptoethanol, in the presence of IL-3 (GENZYME) or WEHI-3 cell conditioned culture medium (WEHI-3CM), for no less than 3 weeks, to obtain spleen-derived cultured mast cells (SMC). In a 6-well plate, NIH-3T3 (Riken Cell Bank) fibroblasts were cultured until confluency; the SMC were suspended in the above-mentioned culture medium, not containing IL-3 and WEHI-3CM, but containing 1 μg/mL of the fusion protein of the present invention, and inoculated at $3 \times 10^5$. Every 2 to 3 days, the culture medium was replaced with fresh media. After culturing at 37° C. for 15 days, the mast cell count, histamine quantity, and chymase activity were measured. The various experimental systems are shown in Table 7.

TABLE 7

| Experimental system | Fibroblasts | Mast cell | Fusion protein |
| --- | --- | --- | --- |
| A | present | Normal mast cells | No addition |
| B | present | Same as above | His Tag-PTD-MITF mi variant |
| C | present | Same as above | His Tag-PTD-MITF wh variant |
| D | present | mi mast cells (mi/mi SMC) | No addition |

Histamine was quantified by an RIA method (Eiken Chemical). Measurement of the chymase activity inside granules was performed using a specific synthetic substrate, N-succinyl-Ala-Ala-Pro-Phe-pNA (Sigma). The results are shown in Table 8.

TABLE 8

| | Count of mast cells (counts/well) | Chymase activity (mOD/minute/well) | Histamine (ng/well) |
| --- | --- | --- | --- |
| A | $3 \times 10^4$ | 14 | 1.05 |
| B | $1 \times 10^4$ | 4 | 0.25 |
| C | $7 \times 10^3$ | 3 | 0.2 |
| D | $8 \times 10^2$ | 0 | 0.03 |

When fibroblasts and normal mast cells were co-cultured, the mast cells survived for a long period of time. Furthermore, mi mast cells which were artificially constructed, having an anomaly in MITF(mi/ml SMC, which do not exist naturally) died within 2 weeks due to apoptosis in a co-culture with fibroblasts. When the fusion protein of the present invention (mi variant type and wh variant type) was added to a co-culture of normal mast cells and fibroblasts, survival of mast cells was inhibited, and most died after 2 weeks in the same manner as with the mi mast cells. A low count of mast cells was also confirmed by the decrease in the quantity of histamine and chymase activity. The result suggests that the fusion protein of the present invention induces apoptosis in mature mast cells.

Experimental Example 4

The influence of the concentration at which the fusion protein of the present invention is added was examined. An MC/9 mast cell strain (obtained from ATCC) was incubated on ice for 1 hour in an FACS staining buffer solution (Dulbecco's PBS containing 0.1% bovine serum albumin and 0.1% sodium azide) in the presence or the absence of a fusion protein comprising an FITC-labeled His Tag-PTD-MITF wh variant. After washing, pyridium iodide was added to gate out the dead cells, and this was analyzed with the FACS Calibur (above-described). Results are shown in Table 9.

TABLE 9

| Concentration of added fusion protein | Peak position of fluorescence intensity |
| --- | --- |
| 0 (μg/mL) | 2.5 |
| 2.5 | 3.5 |

TABLE 9-continued

| Concentration of added fusion protein | Peak position of fluorescence intensity |
|---|---|
| 12.6 | 7 |
| 63 | 22 |

From results of Table 9, it is understood that, depending on the concentration at which the fusion protein of the present invention is added, the fusion protein translocated into cells at higher concentrations.

Example 2

His Tag-PTD-HLH

1) Construction of the Expression Vector

Figure 2:
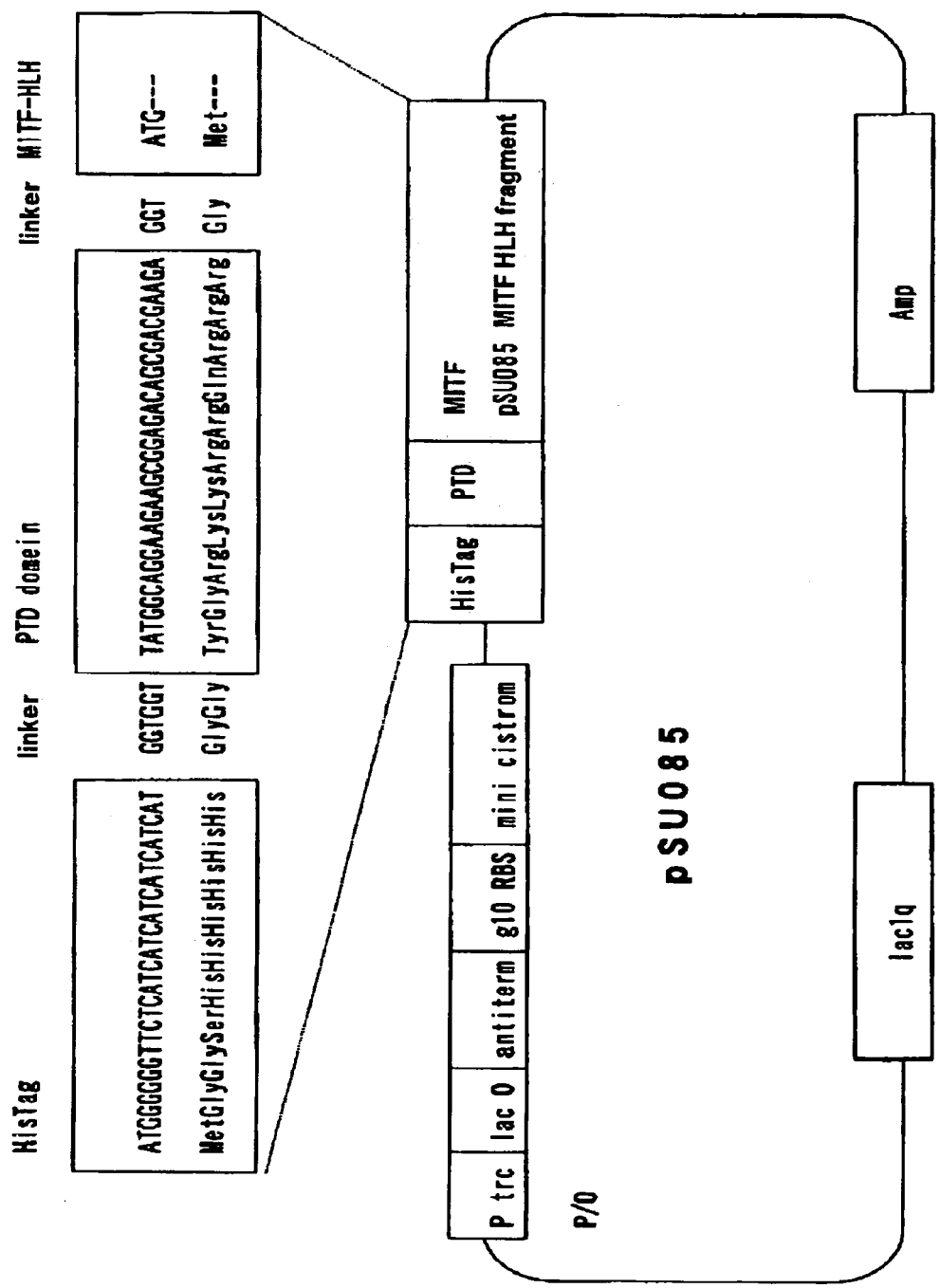
FIG. 2 schematically illustrates the structure of a fusion protein of the present invention (HLH form) and a plasmid pSU085 (HLH form/pTrcHisB) that expresses the fusion path. A portion of the fusion protein SEQ ID NO. 29 and the DNA that codes for the portion of the fusion protein SEQ. ID NO. 28 are also illustrated.

A normal M-type MITF (pSU054) was used as the template for the construction of the expression vector. For the HLH fragment, a region corresponding to N-terminal residues 196 to 285 of the M-type was amplified by the PCR method. His Tag, PTD, and the recognition sequence for the restriction endonuclease NcoI were added on the N-terminal side of the amplified fragment, using primers (Tat1, Tat2, Tat3, and HLH F). Furthermore, the recognition sequence for the restriction endonuclease XbaI was added on the C-terminal side. The amplified fragment was digested with NcoI+XbaI and replaced with the NcoI–XbaI region of pSU081 constructed in Example 1. The amplified fragment was TA-cloned, and it was verified that the base sequence was correct. The constructed vector, pSU085, comprises the lac promoter, the DNA for a His Tag-PTD-HLH region fusion protein, and $amp^r$ (FIG. 2).

A primer HLHF has the following base sequence.

HLHF (SEQ ID NO: 25): GCGACGAAGAGGTATGT-TGGCTAAAGAGAGG

2) The Fusion Protein was Produced and Purified as in Example 1.

Example 3

His Tag-PTD-A-Type N-terminal Region of MITF

1) Construction of the Expression Vector

Figure 3:
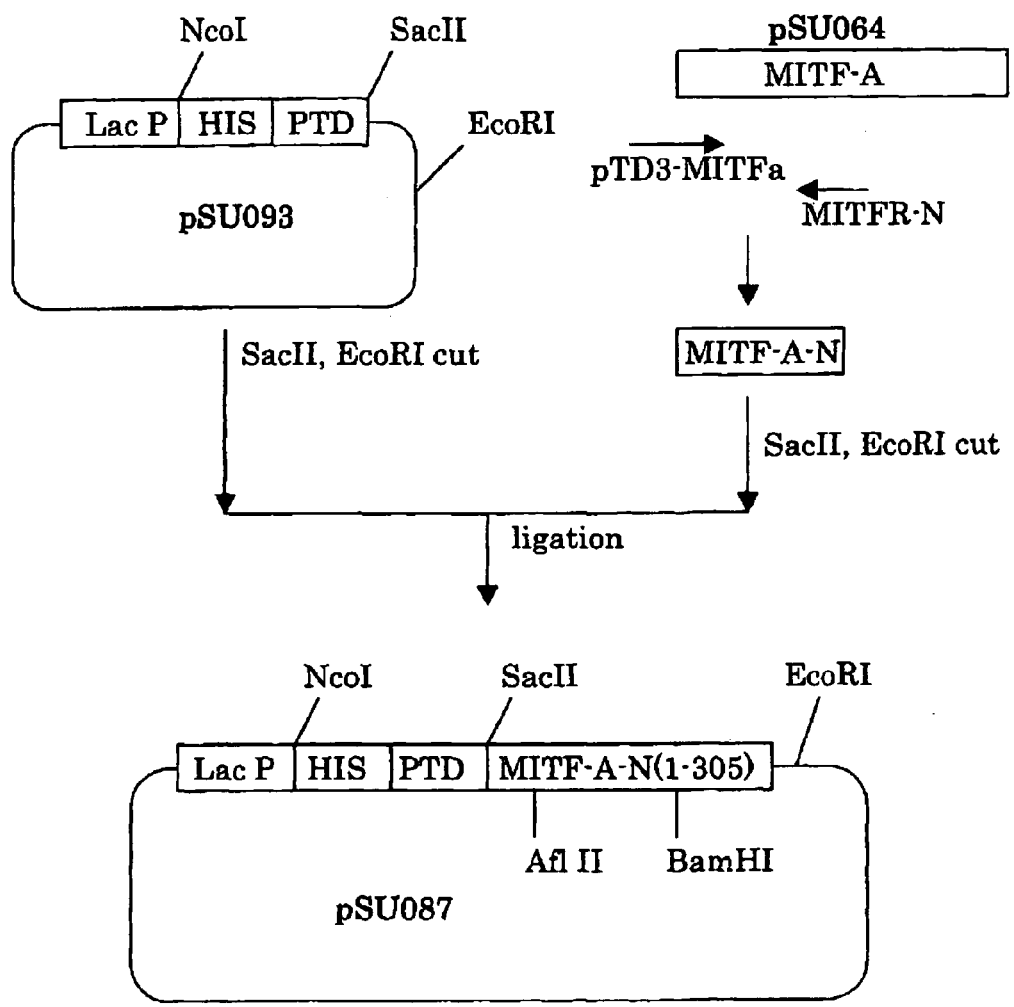
FIG. 3 schematically illustrates a procedure for constructing a plasmid pSU087 (A-type N-terminal region/pSU093) that expresses a fusion protein of the present invention (A-type N-terminal region).

PCR was carried out using two types of primers (pTD3-MITF a and MITF R—N), with pSU064 (A-type MITF/pcDNA3, see WO 01/66735) as the template to amplify the N-terminal region (N-terminal amino acids 1 to 305). A SacII site at the 5' end of the pTD3-MITFa and an EcoRI site at the 5' end of MITF R—N were added. The amplified fragment was digested by SacII+EcoRI and inserted between the same sites on pSU093 (PTD cassette expression vector with pTrcHis as the basic scaffold) (FIG. 3). In the constructed expression vector pSU087, DNA fragments are connected in the His Tag-PTD-A-type N-terminal region (of MITF), and the fusion protein is expressed under the regulation of the lac promoter.

Primers had following base sequences.

pTD3-MITF a (SEQ ID NO: 26): CGCCGCGGAATG-CAGTCCGAATCGGGAATC

MITF R-N (SEQ ID NO: 27): GAATTCACTATGCTCT-TGCTTCAGACTCTGTGGGG

2) After producing the fusion protein according to Example 1, purification thereof was performed using a TALON (product name; CLONTECH) instead of the Ni-agarose. The purified product was prepared as a 10% glycerol/PBS solution.

Example 4

Figure 4:
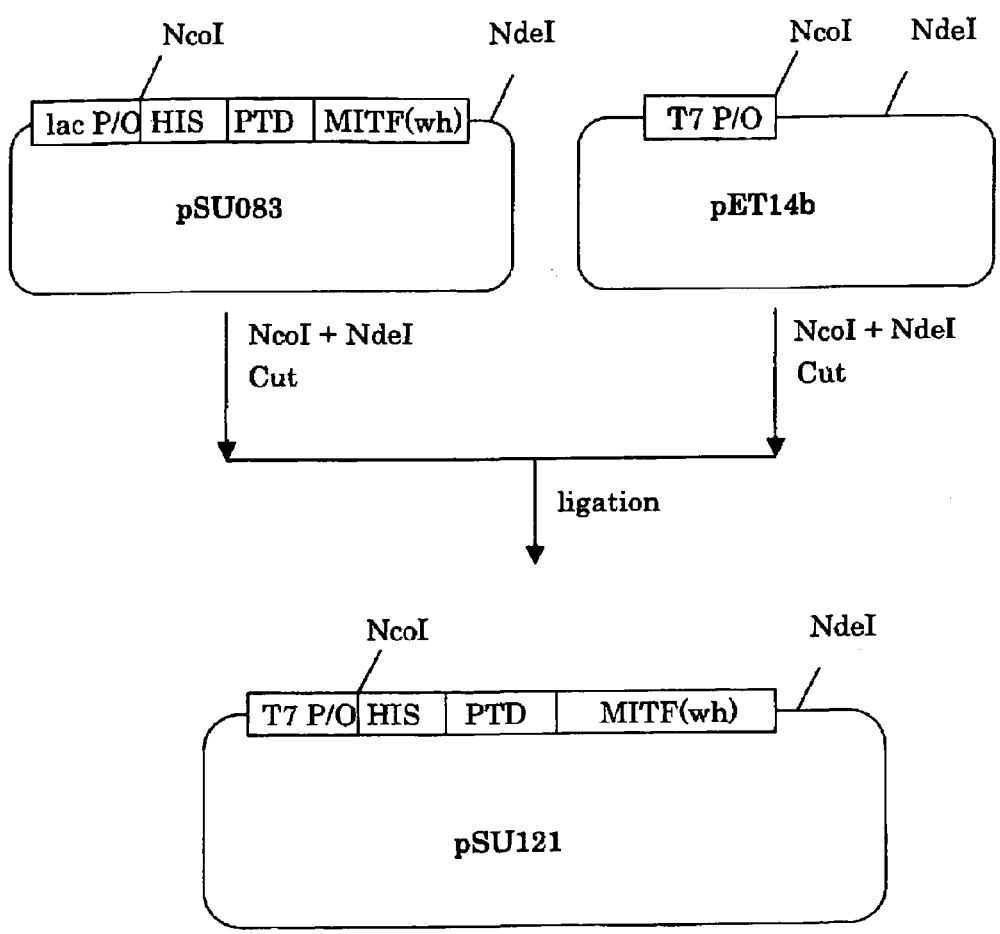
FIG. 4 schematically illustrates a procedure for constructing a plasmid pSU121 (wh form/pET14) that expresses a fusion protein of the present invention (wh form).

Construction of an Expression Vector Using pET14b pSU083 (wh form) NcoI-NdeI fragment and same region in pET14b (made by linking T7 promoter, His Tag, and $amp^r$; Takara) were exchanged to construct the expression vector pSU121 (FIG. 4). This pSU121 has the His Tag, the PTD sequence, and the wh type MITF connected downstream of a T7 promoter and expresses the fusion protein (His Tag-PTD-wh type MITF) under the regulation of the T7 promoter inside *Escherichia coli* cells.

*Escherichia coli* was cultured in a flask to produce the fusion protein (wh form), according to Example 1. This was purified using Ni—NTA agarose according to Example 1, whereafter urea removal processing was carried out using a Slide-A-Dialyzer (Pierce). A 290 mM sorbitol, 10 μM EDTA, 1 mM tris-hydroxymethyl-aminomethane buffer solution (pH 8) was used as a solvent. Approximately 10 mg of fusion protein was purified per liter of culture solution.

Example 5

Purification Process (HLH)

The fusion protein (HLH form) was eluted from a Q-Sepharose column with 1 M NaCl/20 mM HEPES (pH 8), and recovered fractions were buffer-exchanged with PBS using a PD-10 column (Pharmacia) prior to use.

Example 6

High-Density Culture (wh form)

The expression vector pSU083 was introduced into HB101 strain *Escherichia coli* to prepare transformants. This was cultured using EBM0010010 culture medium (ampicillin added) in a jar fermenter at 37° C. for 16 hours to produce the fusion protein. Purification was performed according to Example 1.

Example 7

High-Density Culture (HLH)

The fusion protein was produced using pSU085 according to Example 6. In carrying out purification according to Example 1, the following points were modified: 6 M guanidine hydrochloride was used instead of 8 M urea during Ni—NTA agarose treatment, and instead of the anion exchange treatment, a 3000 molecular weight cutoff membrane was used to concentrate the protein; then, this was desalted over a PD-10 column (Pharmacia) equilibrated with 0.5 M NaCl/20 mM HEPES (pH 8). This was dialyzed against 0.5 M NaCl/20 mM HEPES (pH 7.4), aliquated, and stored at −80° C. For in vivo use, this was diluted to obtain NaCl concentration of 0.15 M and then used.

Formulation Example 2

A composition was prepared, comprising the fusion protein, 10% glycerol, and PBS.

Formulation Example 3

This was prepared as a solution of fusion protein, 0.15–1 M NaCl, and 20 mM HEPES (pH 7.4–8).

Experimental Example 5 (Purification Result)

Various fusion proteins were purified from *Escherichia coli* cells; molecular weights and yields thereof (per 4-L flask culture) are shown in Table 10.

TABLE 10

| Fusion protein | Molecular weight (kDa) | Yields (μg) |
|---|---|---|
| mi form | 50 | 630 |
| wh form | 50 | 400 |
| HLH form | 14 | 130 |

The molecular weight of the fusion protein (A-type N-terminal region) was 37 kDa.

Experimental Example 6 (In Vitro Inhibition)

Experiments were carried out according to Experimental Example 3. After the action of 10 nM fusion protein for 17 days, the mast cell count, histamine, tryptase, and chymase were measured. Results are shown in Table 11.

TABLE 11

| | HLH series | Vehicle (solvent alone) |
|---|---|---|
| Count of mast cells (cells/well) | 6 ± 1** (×10⁴) | 25 ± 1 (×10⁴) |
| histamine (ng/well) | 52 ± 4** | 90 ± 4 |
| tryptase (mOD/minute) | 2.3 ± 0.4** | 10.6 ± 1.2 |
| chymase (mOD/minute) | 0.23 ± 0.08** | 0.78 ± 0.10 |

In the Table, ** indicates that there is a significant difference with respect to the solvent group by the student's test at p<0.05. Furthermore, similarly, * indicates that there is a significant difference at p<0.01. Same hereinafter.

Experimental Example 7 (Same as Above)

Experiments were carried out according to Experimental Example 3. After the action of 20 nM fusion protein for 15 days, a ratio of mast cells was measured. Results are shown in Table 12. The fusion protein of the present invention suppressed survival of mast cells.

TABLE 12

| Fusion protein | Ratio of mast cells (%) |
|---|---|
| mi form | 0.9 ± 0.1** |
| wh form | 0.7 ± 0.2** |
| HLH form | 0.8 ± 0.1** |
| Vehicle | 1.4 ± 0.1** |

Experimental Example 8 (Same as Above)

1) Experiments were carried out according to Experimental Example 2. The count of mast cells was determined when the fusion protein was added to mouse bone marrow cells (2×10⁶/well) in the presence of SCF and cultured for 28 days. The number of wells was 3. Results are shown in Table 13.

TABLE 13

| Fusion protein | Addition concentration | count of mast cells |
|---|---|---|
| vehicle (PBS) | | 8 × 10⁶ |
| wh form | 40 (nM) | 3 × 10⁵ |
| HLH form | 70 | 3 × 10⁵ |

2) Experiments were carried out according to 1). The concentration of fusion protein added was 2.5 nM. Histamine concentration and chymase activity were determined. Results are shown in Table 14.

TABLE 14

| Histamine (ng/mL) | HLH form | 280 ± 40** |
| | vehicle | 740 ± 40 |
| chymase (mOD/minute) | mi type | 0.9 ± 0.2* |
| | HLH type | 0.6 ± 0.2** |
| | vehicle | 1.8 ± 0.2 |

3) Experiments were carried out according to 1). The concentration of fusion protein added was 2.5–20 nM. Cell counts and chymase activity were determined. The number of experiments was 2. Results are shown in Table 15.

TABLE 15

| | Cell count | | Chymase (mOD/minute) | |
|---|---|---|---|---|
| Fusion protein | A-type N-terminus | HLH | A-type N-terminus | HLH |
| vehicle | 10 × 10⁶ | 10 × 10⁶ | 10 | 10 |
| 2.5 (nM) | 0.3 × 10⁶ | 5 × 10⁶ | 0.2 | 3 |
| 5 | 0.2 × 10⁶ | 6 × 10⁶ | 0.05 | 1 |
| 10 | 0.4 × 10⁶ | 1 × 10⁶ | 0.06 | 0.09 |
| 20 | 0.4 × 10⁶ | 0.6 × 10⁶ | 0.03 | 0.03 |

Experimental Example 9
(Effect on Human Mast Cells)

1) A density of 2×10⁴/well human CD34-positive bone marrow cells (BioWhittaker) were cultured for 9 weeks, replacing half the quantity of a culture solution to which SCF (100 ng/ml), IL-6 (100 ng/ml), IL-10 (10 ng/ml), and fusion protein (HLH type) were added once a week; and cell counts, as well as chymase activity, and quantity of histamine in the collected cell lysate were measured. The culture solution used was Media 1 containing 5% FCS (IBL Co., Ltd.). The number of experiments was 3. Results were that the fusion protein of the present invention inhibited human mast cell differentiation (Table 16).

TABLE 16

| | Fusion protein | Vehicle |
|---|---|---|
| cell count (at maximum) | 6 × 10⁵ | 4 × 10⁵ |
| chymase (mOD/minute) | 0.07 ± 0.02 | 0.25 ± 0.07 |
| histamine (ng/mL) | 40 ± 20 | 70 ± 15 |

2) Human CD34-positive bone marrow cells were cultured for 8 weeks according to 1) in the presence of cytokines to prepare partially differentiated immature mast cells. Cells were temporarily recovered, washed by centrifugation, and used to inoculate a culture solution on a new plate at 7×10⁵/well; culturing was continued, using the same culture solution (containing the above-mentioned cytokines) to which fusion protein was added (10 or 50 nM of HLH form were added).

Once a week, half the quantity of the culture solution was replaced. After 2 weeks of culture, the cell count, chymase activity, and quantity of histamine were measured. Furthermore, the cells were stained with PE-labeled anti c-kit antibody (or PE-labeled control antibody) and analyzed by FACS. The results were that the fusion protein of the present invention had an effect on immature mast cells, inhibiting c-kit expression and inhibiting the maturation of human mast cells (Table 17).

TABLE 17

|  | Immediately before culture | Fusion protein 50 nM | Same 10 nM | Vehicle |
|---|---|---|---|---|
| chymase (mOD/minute) | 0.08 | 0.03 | 0.06 | 0.15 |
| histamine (ng/mL) | 290 | 200 | 330 | 570 |
| peak position of FACS |  | $8 \times 10$ | $1 \times 10^2$ | $2 \times 10^2$ |

3) Human CD34-positive bone marrow cells were cultured according to 1) in the presence of cytokines for 12 weeks to prepare completely differentiated mature mast cells. Cells were temporarily collected, washed by centrifugation, and used to inoculate in a culture solution on a new plate at $2.4 \times 10^4$/well; culture was continued, using the same culture solution (containing the above-mentioned cytokines) to which fusion protein was added (2, 10, or 50 nM of HLH form were added). Once a week, half the quantity of the culture solution was replaced. After 3 weeks of culture, the cell count and the quantity of histamine were measured. Results were that the fusion protein of the present invention decreased the quantity of histamine in a concentration-dependent manner, suppressing the function of the cultured mature mast cells from human bone marrow (Table 18).

TABLE 18

| Fusion protein (nM) | Histamine (ng/mL) |
|---|---|
| solvent only | 600 ± 20 |
| 2 | 520 ± 50 |
| 10 | 370 ± 10 |
| 50 | 300 ± 10 |

Experimental Example 10 (In Vivo Inhibition)

1) A dose of 60 µg fusion protein (wh form) in 200 µL PBS was administered into peritoneal cavities of C57BU6 mice 3 times a week for 4 weeks. The day after final administration, peritoneal cells were collected, and following items were measured. The number of mice/group was 4. Results from the 4-week administration are shown in Table 19.

Total cell count: This was measured using coulter counter or hemocytometric counter.

Mast cells: A smear specimen was stained positives was calculated.

Histamine: Triton X-100 was added to a cell suspension of peritoneal cavity to prepare a lysate, and the lysate was measured with an ELISA kit.

Cells positive for both c-kit and IgE receptors: Collected peritoneal cavity cells were double-stained with PE-labeled anti c-kit antibody and mouse IgE/biotin-labeled anti-IgE antibody/APC-labeled streptavidin and analyzed by FACS.

TABLE 19

|  | Vehicle group | Fusion protein | Significant difference |
|---|---|---|---|
| Ratio of mast cells (%) | 0.8 | 0.4 | 0.0394 |
| Count of mast cells | $0.3 \times 10^5$ | $0.17 \times 10^5$ | 0.2784 |
| Frequency of c-kit$^+$ IgER$^+$ cells (%) | 0.6 | 0.4 | 0.3080 |
| Count of same cells | $2.3 \times 10^5$ | $1.4 \times 10^5$ | 0.2214 |
| histamine (ng/$10^6$ cells) | 42 | 11 | 0.0510 |

2) A quantity of 10 or 50 µg of fusion protein (wh form, both in 200 µL of vehicle) was administered into peritoneal cavities of mice for 2 weeks. The number of mice/group was 10. Each item was measured as in 1). Results are shown in Table 20.

TABLE 20

|  | Vehicle group | Fusion protein 10 µg | Fusion protein 50 µg |
|---|---|---|---|
| Count of total cells | 9 ± 1 ($\times 10^6$) | 11 ± 1 ($\times 10^6$) | 12 ± 1* ($\times 10^6$) |
| Ratio of mast cells (%) | 0.9 ± 0.2 | 0.4 ± 0.1** | 0.2 ± 0.1** |
| Ratio of both-positive mast cells (%) | 0.48 ± 0.10 | 0.29 ± 0.05 | 0.20 ± 0.04** |
| Fluorescence intensity of c-kit average | 900 ± 50 | 680 ± 30** | 670 ± 30** |

3) A quantity of 10 µg of fusion protein (HLH form) in 350 µL of vehicle was administered into peritoneal cavities of mice for 13 days. The mast cell count and the quantity of histamine were measured according to 1). Results are shown in Table 21.

TABLE 21

|  | Vehicle group | Fusion protein |
|---|---|---|
| mast cell count | 1.9 ± 0.6 ($\times 10^4$) | 0.1 ± 0.1** ($\times 10^4$) |
| histamine (nM) | 6.7 ± 2.0 | 0.7 ± 0.5* |

The fusion protein of the present invention (wh form, HLH form) decreased the in vivo mast cell count in both experimental systems.

INDUSTRIAL APPLICABILITY

According to the present invention, cell death of mast cells can be induced using MITF variants.

Therefore, it is possible to provide the clinical field with an agent useful in the prevention and treatment of various diseases in which mast cells are implicated.

Note that the present application claims priority from Japanese Patent Application No. 2001-204567.

The invention claimed is:

1. A cell death inducer for mast cells, wherein said cell death inducer having a fusion protein comprising a PTD (protein transduction domain) and a MITF (microphthalmia-associated transcription factor) variant.

2. The cell death inducer according to claim 1, wherein the fusion protein further comprises a His Tag.

3. The cell death inducer according to claim 1, wherein the MITF variant is an MITF mi variant, wh variant, HLH (basic-helix-loop-helix/leucine zipper) fragment, or an A-type N-terminal region (1-305) fragment (SEQ ID NO: 21), and the PTD is a TAT-derived peptide.

4. The cell death inducer according to claim 1, wherein the fusion protein has the amino acid sequence shown by SEQ ID NO: 11, 13, 15, or 23.

5. The cell death inducer according to claim 1, wherein the fusion protein is treated with a denaturing agent (chaotrophic agent) and subsequently removing said denaturing agent.

6. The cell death inducer according to claim 5, wherein the denaturing agent is urea, guanidine hydrochloride, or thiocyanate.

7. A pharmaceutical composition comprising the cell death inducer according to claim 1 and a pharmacologically acceptable carrier.

8. A DNA coding for the cell death inducer according to claim 1.

9. The DNA according to claim 8, wherein the fusion protein has the amino acid sequence shown in SEQ ID NO: 11, 13, 15, or 23.

10. The DNA according to claim 8, wherein said DNA has the base sequence shown in SEQ ID NO: 12, 14, 16, or 24.

11. A vector comprising the DNA of claim 8.

12. A host cell comprising the vector of claim 11.

13. The host cell of claim 12, wherein said host cell is *E. coli*.

14. A method for producing a fusion protein comprising a PTD (protein transduction domain) and a MITF (microphthalmia-associated transcription factor) variant, wherein said method comprises culturing the host cell of claim 12 under conditions that allow the expression of the fusion protein, and isolating the fusion protein therefrom.

15. The method of claim 14, further comprising denaturing the fusion protein with a denaturing agent, passing the fusion protein over a Ni column, and removing the denaturing agent from the fusion protein.

16. The method according to claim 15, wherein the denaturing agent is urea, guanidine hydrochloride, or thiocyanate.

17. The method according to claim 15, wherein the denaturing agent is added at a concentration of 1–10 M.

18. The method according to claim 15, wherein the denaturing agent is removed by anion exchange or by dialysis.

19. A fusion protein comprising a His Tag, a PTD (protein transduction domain), and an MITF (microphthalmia-associated transcription factor) variant, wherein the MITF variant is an MITF mi variant, wh variant, HLH (basic-helix-loop-helix/leucine zipper) fragment, or an A-type-N-terminal region (1-305) fragment (SEQ ID NO: 21), and the PTD is a TAT-derived peptide.

20. The fusion protein according to claim 19, wherein the fusion protein has the amino acid sequence shown in SEQ ID NO: 11, 13, 15, or 23.

21. A pharmaceutical composition comprising the fusion protein according to claim 19 and a pharmacologically acceptable carrier.

22. The pharmaceutical composition according to claim 21, wherein the concentration of the fusion protein is 0.1–100 µg/ml or 0.1–100 nM.

23. A DNA coding for the fusion protein according to claim 19.

24. The DNA according to claim 23, wherein the fusion protein has the amino acid sequence shown in SEQ ID NO: 11, 13, 15, or 23.

25. The DNA according to claim 23, wherein said DNA has the base sequence shown In SEQ ID NO: 12, 14, 16, or 24.

26. A vector comprising the DNA of claim 23.

27. A host cell comprising the vector of claim 26.

28. The host cell of claim 27, wherein said host cell is *E. coli*.

29. A method for producing a fusion protein comprising a His Tag, a PTD (protein transduction domain), and an MITF (micropthalmia-associated transcription factor) variant, wherein the MITF variant is an MITF mi variant, wh variant, HLH (basic-helix-loop-helix/leucine zipper) fragment, or an A-type-N-terminal region (1-305) fragment (SEQ ID NO: 21), and the PTD is a TAT-derived peptide, said method comprising culturing the host cell of claim 27 under conditions that allow the expression of the fusion protein, and isolating the fusion protein therefrom.

30. The method claim 29, further comprising denaturing the fusion protein with a denaturing agent, passing the fusion protein over a Ni column, and removing the denaturing agent from the fusion protein.

31. The method according to claim 30, wherein the denaturing agent is urea, guanidine hydrochloride, or thiocyanate.

32. The method according to claim 30, wherein the denaturing agent is added at 1–10 M.

33. The method according to claim 30, wherein the denaturing agent is removed by anion exchange or by dialysis.

34. A therapeutic agent formulated for treating a disease in which mast cells are implicated, said agent having a fusion protein comprising a PTD (protein transduction domain) and a MITF (microphthalmia-associated transcription factor) variant.

35. The therapeutic agent according to claim 34, wherein the fusion protein further comprises a His Tag.

36. The therapeutic agent according to claim 34, wherein the disease in which mast cells are implicated is an allergy, asthma, an autoimmune disease, pulmonary fibrosis, a carcinoma, mastocytoma, or mastoeytosis.

37. A method for inducing cell death in mast cells, said method comprising administering an effective dose of a fusion protein comprising a PTD (protein transduction domain) and a MITF (microphthalmia-associated transcription factor) variant to a subject having an allergy, asthma, an autoimmune disease, pulmonary fibrosis, a carcinoma, mastocytoma, or mastocytosis, in which mast cells have been implicated, and wherein the disease is alleviated.

38. The method according to claim 37, wherein the fusion protein further comprises a His Tag.

39. The method according to claim 37, wherein the fusion protein is administered is intravenously, subcutaneously, intramuscularly, percutaneously, or tracheobronchially.

40. The method according to claim 37, wherein the fusion protein is administered at a dose of 10 µg–50 mg.

\* \* \* \* \*

UNITED STATES PATENT AND TRADEMARK OFFICE
CERTIFICATE OF CORRECTION

| | |
|---|---|
| PATENT NO. | : 7,217,539 B2 |
| APPLICATION NO. | : 10/482793 |
| DATED | : May 15, 2007 |
| INVENTOR(S) | : Naito et al. |

Page 1 of 1

It is certified that error appears in the above-identified patent and that said Letters Patent is hereby corrected as shown below:

Column 60, line 17, "mastoeytosis" should read --mastocytosis--.

Signed and Sealed this

Third Day of July, 2007

JON W. DUDAS
*Director of the United States Patent and Trademark Office*